US010829372B2

(12) United States Patent
Sookraj et al.

(10) Patent No.: US 10,829,372 B2
(45) Date of Patent: Nov. 10, 2020

(54) INTEGRATED METHODS FOR CHEMICAL SYNTHESIS

(71) Applicant: Novomer, Inc., Rochester, NY (US)

(72) Inventors: Sadesh H. Sookraj, Cambridge, MA (US); Michael A. Slowik, Waltham, MA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 16/787,510

(22) Filed: Feb. 11, 2020

(65) Prior Publication Data

US 2020/0172396 A1 Jun. 4, 2020

Related U.S. Application Data

(63) Continuation of application No. 15/314,429, filed as application No. PCT/US2015/033232 on May 29, 2015, now Pat. No. 10,597,294.
(Continued)

(51) Int. Cl.
*H01M 8/0612* (2016.01)
*H01M 8/0668* (2016.01)
(Continued)

(52) U.S. Cl.
CPC ............... *C01B 3/50* (2013.01); *B01J 31/00* (2013.01); *C07C 1/20* (2013.01); *C07C 29/149* (2013.01);
(Continued)

(58) Field of Classification Search
None
See application file for complete search history.

(56) References Cited

U.S. PATENT DOCUMENTS 2,245,404 A 6/1941 Kise et al.
2,302,321 A 11/1942 Hopff et al.
(Continued)

FOREIGN PATENT DOCUMENTS

CN 103822811 A 5/2014
EP 352850 A1 1/1990
(Continued)

OTHER PUBLICATIONS

Getzler et al., "Synthesis of ?-Lactones: A Highly Active and Selective Catalyst for Epoxide Carbonylation", Journal of the American Chemical Society. vol. 124, No. 7, 2002, pp. 1174-1175.
(Continued)

*Primary Examiner* — Sarah A. Slifka
(74) *Attorney, Agent, or Firm* — Young Basile Hanlon & MacFarlane, P.C.

(57) ABSTRACT

Among other things, the present invention encompasses the applicant's recognition that epoxide carbonylation can be performed industrially utilizing syngas streams containing hydrogen, carbon monoxide and varying amounts carbon dioxide. Contrary to expectation, the epoxide carbonylation reaction proceeds selectively in the presence of these mixed gas streams and incorporates excess CO in the syngas stream into valuable chemical precursors, resulting in hydrogen streams substantially free of CO. This is economically and environmentally preferable to performing WSGR which releases the excess carbon as CO2. The integrated processes herein therefore provide improved carbon efficiency for processes based on coal or biomass gasification or steam methane reforming.

11 Claims, 6 Drawing Sheets

Related U.S. Application Data

(60) Provisional application No. 62/004,978, filed on May 30, 2014.

(51) Int. Cl.

| | | |
|---|---|---|
| *C01B 3/50* | (2006.01) | |
| *C07D 307/60* | (2006.01) | |
| *C07C 51/09* | (2006.01) | |
| *C07C 29/151* | (2006.01) | |
| *C10G 2/00* | (2006.01) | |
| *C07C 29/149* | (2006.01) | |
| *C07C 1/20* | (2006.01) | |
| *B01J 31/00* | (2006.01) | |
| *C07D 305/12* | (2006.01) | |
| *B01J 31/20* | (2006.01) | |

(52) U.S. Cl.
CPC .......... *C07C 29/1518* (2013.01); *C07C 51/09* (2013.01); *C07D 305/12* (2013.01); *C07D 307/60* (2013.01); *C10G 2/30* (2013.01); *C10G 2/32* (2013.01); *H01M 8/0625* (2013.01); *H01M 8/0668* (2013.01); *B01J 31/20* (2013.01); *B01J 2231/321* (2013.01); *B01J 2531/025* (2013.01); *B01J 2531/72* (2013.01); *B01J 2531/822* (2013.01); *B01J 2531/827* (2013.01); *B01J 2531/842* (2013.01); *B01J 2531/845* (2013.01); *C01B 2203/04* (2013.01); *C01B 2203/0435* (2013.01); *C01B 2203/062* (2013.01); *C01B 2203/065* (2013.01); *C01B 2203/066* (2013.01); *Y02P 20/10* (2015.11); *Y02P 20/52* (2015.11); *Y02P 30/20* (2015.11); *Y02P 30/40* (2015.11)

(56) References Cited

U.S. PATENT DOCUMENTS

| | | |
|---|---|---|
| 2,469,704 A | 5/1949 | Stone |
| 2,526,554 A | 10/1950 | Gresham et al. |
| 3,002,017 A | 9/1961 | Wearsch et al. |
| 3,326,938 A | 6/1967 | Wagner |
| 3,751,435 A | 8/1973 | van der Ven et al. |
| 3,800,006 A | 3/1974 | Katayama et al. |
| 3,885,155 A | 5/1975 | Anbar |
| 4,026,967 A | 5/1977 | Flexman, Jr. et al. |
| 4,081,253 A | 3/1978 | Marion |
| 4,427,884 A | 1/1984 | Anbar et al. |
| 4,590,293 A | 5/1986 | Pascoe |
| 4,873,378 A | 10/1989 | Murphy et al. |
| 4,973,841 A | 11/1990 | Purser |
| 5,096,470 A | 3/1992 | Krishnamurthy |
| 5,198,578 A | 3/1993 | Etzkorn et al. |
| 5,310,948 A | 5/1994 | Drent et al. |
| 5,359,081 A | 10/1994 | Drent et al. |
| 5,438,194 A | 8/1995 | Koudijs et al. |
| 5,661,299 A | 8/1997 | Purser |
| 5,731,252 A | 3/1998 | Warner et al. |
| 6,147,126 A | 11/2000 | DeGeorge et al. |
| 6,392,078 B1 | 5/2002 | Ryu et al. |
| 6,492,535 B1 | 12/2002 | Castiglioni et al. |
| 6,573,340 B1 | 6/2003 | Khemani et al. |
| 6,773,578 B1 | 8/2004 | O'Rear et al. |
| 6,852,865 B2 | 2/2005 | Coates et al. |
| 6,916,951 B2 | 7/2005 | Tustin et al. |
| 8,445,703 B2 | 5/2013 | Allen et al. |
| 8,481,756 B1 | 7/2013 | Coates et al. |
| 8,796,475 B2 | 8/2014 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2003/0098274 A1 | 5/2003 | Lee et al. |
| 2003/0162961 A1 | 8/2003 | Coates et al. |
| 2004/0102532 A1 | 5/2004 | Landis et al. |
| 2005/0014977 A1 | 1/2005 | Drent et al. |
| 2005/0196343 A1 | 9/2005 | Reddy et al. |
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2007/0155984 A1 | 7/2007 | Sielcken et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0299032 A1 | 12/2009 | Allen |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0209775 A1 | 8/2013 | Allen et al. |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |

(56) References Cited

U.S. PATENT DOCUMENTS

| | | |
|---|---|---|
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0002400 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| EP | 441447 A1 | 8/1991 |
| EP | 2325214 A1 | 5/2011 |
| GB | 762138 A | 11/1956 |
| JP | 57-14596 A | 1/1982 |
| WO | 2002/09781 A2 | 2/2002 |
| WO | 2003/050154 A2 | 6/2003 |
| WO | 2003/074585 A1 | 9/2003 |
| WO | 2004/089923 A1 | 10/2004 |
| WO | 2006/087556 A1 | 8/2006 |
| WO | 2009/155086 A2 | 12/2009 |
| WO | 2010/118128 A1 | 10/2010 |
| WO | 2010/137974 A1 | 12/2010 |
| WO | 2011/063309 A1 | 5/2011 |
| WO | 2011/123558 A1 | 10/2011 |
| WO | 2011/163309 A2 | 12/2011 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/067460 A1 | 5/2013 |
| WO | 2013/068846 A1 | 5/2013 |
| WO | 2013/122905 A1 | 8/2013 |
| WO | 2013/126375 A1 | 8/2013 |
| WO | 2013/180659 A1 | 12/2013 |
| WO | 2013/185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/110321 A1 | 7/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

International Preliminary Report on Patentability received for PCT Patent Application No. PCT/US2015/033232, dated Dec. 15, 2016, 7 Pages.

International Search Report and Written Opinion received for PCT Patent Application No. PCT/US2015/033232, dated Aug. 19, 2015, 8 pages.

Kaesz et al., "Hydride Complexes of the Transition Metals", Chemical Reviews, vol. 72, No. 3, 1972, pp. 231-281.

Schulz, Hans,"Short History and Present Trends of Fischer-Tropsch Synthesis", Applied Catalysis A: General, vol. 186, No. 1-2, Oct. 1999, pp. 3-12.

Trimm et al., "Minimisation of Carbon Monoxide in a Hydrogen Stream for Fuel Cell Application", Applied Catalysis A: General, vol. 296, 2005, pp. 138-148.

Wilen et al., "Strategies in Optical Resolutions", Tetrahedron, vol. 33, 1977, pp. 2725-2736.

Dubinsky et al., "Thermal Degradation of Poly(Acrylic Acid) Containing Copper Nitrate", Polymer Degradation and Stability, vol. 86, 2004, pp. 171-178.

Extended European Search Report received for European Patent Application No. 15799546.5, dated Nov. 24, 2017, 6 pages.

Ganji et al., "In Situ Generation of the Coates Catalyst: A Practical and Versatile Catalytic System for the Carbonylation of Meso-Epoxides", Organic Letters, vol. 13, No. 12, 2011, pp. 3142-3145.

International Preliminary Report on Patentability received for PCT Patent Application No. PCT/US2016/017881, dated Aug. 24, 2017, 7 pages.

International Search Report and Written Opinion received for PCT Patent Application No. PCT/US2016/017875, dated May 6, 2016, 16 pages.

International Search Report and Written Opinion received for PCT Patent Application No. PCT/US2016/017844, dated May 6, 2016, 10 pages.

International Search Report and Written Opinion received for PCT Patent Application No. PCT/US13/25683, dated Apr. 23, 2013, 8 pages.

International Search Report and Written Opinion received for PCT Patent Application No. PCT/US17/23302, dated Jun. 5, 2017, 9 pages.

International Search Report and Written Opinion received for PCT Patent Application No. PCT/US17/23303, dated Jun. 7, 2017, 18 pages.

International Search Report and Written Opinion received for PCT Patent Application No. PCT/US2010/030230, dated Jun. 10, 2010, 17 pages.

International Search Report and Written Opinion received for PCT Patent Application No. PCT/US11/49125, dated Jan. 11, 2012, 10 pages.

International Search Report and Written Opinion received for PCT Patent Application No. PCT/US2012/037675, dated Aug. 9, 2012, 12 pages.

International Search Report and Written Opinion received for PCT Patent Application No. PCT/US2012/061791, dated Feb. 8, 2013, 10 pages.

International Search Report and Written Opinion received for PCT Patent Application No. PCT/US2013/026810, dated Apr. 30, 2013, 8 pages.

International Search Report and Written Opinion received for PCT Patent Application No. PCT/US2013/048238, dated Dec. 3, 2013, 8 pages.

International Search Report and Written Opinion received for PCT Patent Application No. PCT/US2013/049026, dated Dec. 17, 2013, 9 pages.

International Search Report and Written Opinion received for PCT Patent Application No. PCT/US2014/069066, dated Mar. 16, 2015, 10 pages.

(56) References Cited

OTHER PUBLICATIONS

International Search Report and Written Opinion received for PCT Patent Application No. PCT/US2015/020562, dated Jun. 18, 2015, 9 pages.
International Search Report and Written Opinion received for PCT Patent Application No. PCT/US2015/028123, dated Jul. 23, 2015, 7 pages.
International Search Report and Written Opinion received for PCT Patent Application No. PCT/US2015/042124, dated Dec. 15, 2015, 14 pages.
International Search Report and Written Opinion received for PCT Patent Application No. PCT/US2016/017797, dated May 5, 2016, 9 pages.
International Search Report and Written Opinion received for PCT Patent Application No. PCT/US2016/017861, dated Apr. 29, 2016, 25 pages.
International Search Report and Written Opinion received for PCT Patent Application No. PCT/US2016/017868, dated May 2, 2016, 9 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/017881, dated May 2, 2016, 8 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2017/059243, dated Feb. 1, 2018, 10 pages.
Rowley et al., "Catalytic Double Carbonylation of Epoxides to Succinic Anhydrides: Catalyst Discovery, Reaction Scope, and Mechanism", Journal of the American Chemical Society, vol. 129, No. 16, 2007, pp. 4948-4960.
Schechtman et al., "Chemical Synthesis of Isotactic Poly(3-Hydroxyalkanoates)", Polymer Preprints, vol. 40, No. 1, Mar. 1999, pp. 508-509.
Slowik et al., "Catalytic Conversion of Waste Carbon Monoxide to Valuable Chemicals & Materials", Clean Technology, 2010, pp. 283-286.
Stanghellini et al., "Redox Reactions of Metal Carbonyls. I. Kinetics and Mechanism of Disproportionation of Co2 (Co)8 with Piperidine", Inorganica Chimica Acta, vol. 22, 1977, pp. 19-22.
"Understanding Biobased Carbon Content", Society of the Plastics Industry Bioplastics Council, Feb. 2012, pp. 1-12.
Extended European Search Report (includes Supplementary European Search Report and Search Opinion) received for European Patent Application No. 16750026.3, dated Sep. 19, 2018, 11 pages.
Partial Supplementary European Search Report received for European Patent Application No. 16750026.3, dated Jul. 12, 2018, 10 pages.
Non-Final Office Action received for U.S. Appl. No. 15/550,300, dated Dec. 31, 2018, 11 pages.
Ganji et al., "In Situ Generation of the Coatescatalyst: a Practical and Versatile Catalytic System for the Carbonylation of Meso-Epoxides", ChemInform Abstract, vol. 42, No. 39, 2011, 1 page.

INTEGRATED METHODS FOR CHEMICAL SYNTHESIS

CROSS REFERENCE TO RELATED APPLICATION(S)

This disclosure is continuation application of application Ser. No. 15/314,429, filed on Nov. 28, 2019, published as United States Application Publication 2017/0107103, which is a national stage entry of PCT/US2015/33232, filed on May 29, 2015, which claims the benefit of U.S. Provisional Application No. 62/004,978, filed on May 30, 2014, the disclosure of all is hereby incorporated by reference in its entirety.

BACKGROUND OF THE INVENTION

Interest in finding sustainable methods to produce energy and chemicals continues to increase in the face of concerns that anthropogenic carbon emissions may be responsible for global climate change. Among the options being considered is the use of biomass to feed chemical production via the output of gasification reactions. This process has appeal since the processes first developed more than a century ago for coal gasification can be applied to practically any biomass input, and the subsequent conversion of the resulting syngas to fuels or chemicals by well established processes has the potential to provide a diverse range of more sustainable chemical products.

However, a drawback to gasification technology is that it is relatively inefficient in terms of the percentage of the biomass carbon input to the gasifier that is actually incorporated into the desired end products, typically, less than 50%. This is due in large part to the fact that coal and biomass-derived syngas has a low $H_2$ to CO ratio (typically around ~0.7) and must be upgraded by water gas shift reaction (WGSR) prior to utilization in downstream processes such as Fischer Tropsch (FT) or Methanol-to-olefins (MTO) synthesis that typically requires a $H_2$:CO ratio around 2. The water gas shift process entails the reaction of a water molecule with a carbon monoxide molecule (from the syngas), producing $CO_2$ and hydrogen.

The resulting $CO_2$ (22 kg $CO_2$ per kg of $H_2$ produced) is emitted to the atmosphere and erodes the carbon efficiency and environmental benefit of biomass gasification technologies. Furthermore, the water required for the WGSR process could otherwise be consumed or used in agriculture, and the residual water returned from the process is unfit for those uses without further purification.

A related situation exists for conversion of carbonaceous feedstocks to produce pure hydrogen streams for use in chemical production (e.g. ammonia production) or for use as a fuel. Here, the preferred process is methane steam reforming (MSR): $CH_4 + H_2O \rightleftharpoons CO + 3\ H_2$. Again, the gas stream produced by MSR is typically treated by WGSR to increase the hydrogen content. However, rather than being converted to valuable chemicals, the CO from MSR is instead converted to $CO_2$ which is then released to the atmosphere.

The present invention provides solutions to these and related problems.

SUMMARY OF THE INVENTION

Among other things, the present invention encompasses the applicant's recognition that epoxide carbonylation can be performed industrially utilizing syngas streams containing hydrogen, carbon monoxide and varying amounts carbon dioxide. Contrary to expectation, the epoxide carbonylation reaction proceeds selectively in the presence of these mixed gas streams and incorporates excess CO from the syngas stream into valuable chemical precursors. Where the goal of biomass gasification is to maximize the amount of biomass-derived carbon converted to valuable chemical products, the present invention has the advantage of incorporating the CO present in syngas into those products. This is economically and environmentally preferable to performing WSGR which converts that CO to $CO_2$, which is then lost to the atmosphere. The integrated processes herein therefore provide improved carbon efficiency for processes based on coal or biomass gasification or steam methane reforming.

In one aspect, the present invention provides an integrated process for the conversion of biomass or coal to FT products and commodity chemicals derived from epoxide carbonylation. In certain embodiments, such methods comprise the steps of:
  a) in a first reaction zone, contacting syngas derived from gasification of biomass or coal with an epoxide in the presence of a carbonylation catalyst thereby consuming carbon monoxide from the syngas and producing an epoxide carbonylation product,
  b) recovering an upgraded gas stream from the first reaction zone wherein the upgraded gas stream has a higher hydrogen to carbon monoxide ratio than the starting syngas stream,
  c) in a second reaction zone, utilizing the upgraded gas stream to conduct a second chemical process requiring a hydrogen to carbon monoxide ratio higher than the ratio in the industrial gas stream utilized in step (a).

In certain embodiments of the method above, the second chemical process comprises the utilization of the syngas with a $H_2$:CO ratio of ~2 in a Fischer Tropsch synthesis.

In a second aspect, the present invention provides an integrated process for the production of hydrogen and commodity chemicals derived from epoxide carbonylation. In certain embodiments, such methods comprise the steps of:
  a) in a first reaction zone, contacting a syngas stream derived from biomass or MSW gasification, or a steam reforming process, with an epoxide in the presence of a carbonylation catalyst thereby consuming carbon monoxide from the syngas stream and producing an epoxide carbonylation product,
  b) recovering an upgraded gas stream from the first reaction zone wherein the upgraded gas stream has a higher hydrogen to carbon monoxide ratio than the starting syngas stream, and
  c) in a second reaction zone, utilizing the upgraded gas stream to conduct a second chemical process requiring a hydrogen to carbon monoxide ratio higher than the ratio in the industrial gas stream utilized in step (a).

In certain embodiments, the epoxide carbonylation product produced in step (a) of the methods above is selected from the group consisting of: optionally substituted beta propiolactone, optionally substituted succinic anhydride, and optionally substituted polypropiolactone. In certain embodiments, the epoxide in the methods above is ethylene oxide and the epoxide carbonylation product is selected from the group consisting of: beta propiolactone, succinic anhydride and polypropiolactone. In certain embodiments, the epoxide in the methods above is propylene oxide and the epoxide carbonylation product is selected from the group consisting of: beta butyrolactone, methyl succinic anhydride and poly(3-hydroxy butyrate).

In certain embodiments of the methods above, the syngas stream in step (a) is characterized in that it has an $H_2$ to CO ratio less than 1.2. In certain embodiments, the upgraded gas stream in step (b) is characterized in that it has an $H_2$ to CO ratio greater than 1.9.

In another aspect, the present invention provides an integrated process for the production of hydrogen and commodity chemicals derived from beta lactone carbonylation. In certain embodiments, such methods comprise the steps of:
  a) in a first reaction zone, contacting syngas with a beta propiolactone in the presence of a carbonylation catalyst thereby consuming carbon monoxide from the syngas and producing a succinic anhydride product,
  b) recovering an upgraded gas stream from the first reaction zone wherein the upgraded gas stream has a higher hydrogen to carbon monoxide ratio than the starting syngas stream,
  c) in a second reaction zone, utilizing the upgraded gas stream to conduct a second chemical process requiring a hydrogen to carbon monoxide ratio higher than the ratio in the industrial gas stream utilized in step (a).

In certain embodiments of this aspect, the syngas in step (a) is derived from methane steam reforming (MSR). In certain embodiments, the syngas in step (a) is an upgraded gas stream produced as described in the first two aspects of the methods described above.

In certain embodiments of this aspect, the beta propiolactone carbonylation reaction zone is operated under conditions such that substantially all of the CO in the syngas stream is consumed.

DEFINITIONS

Figure 1:
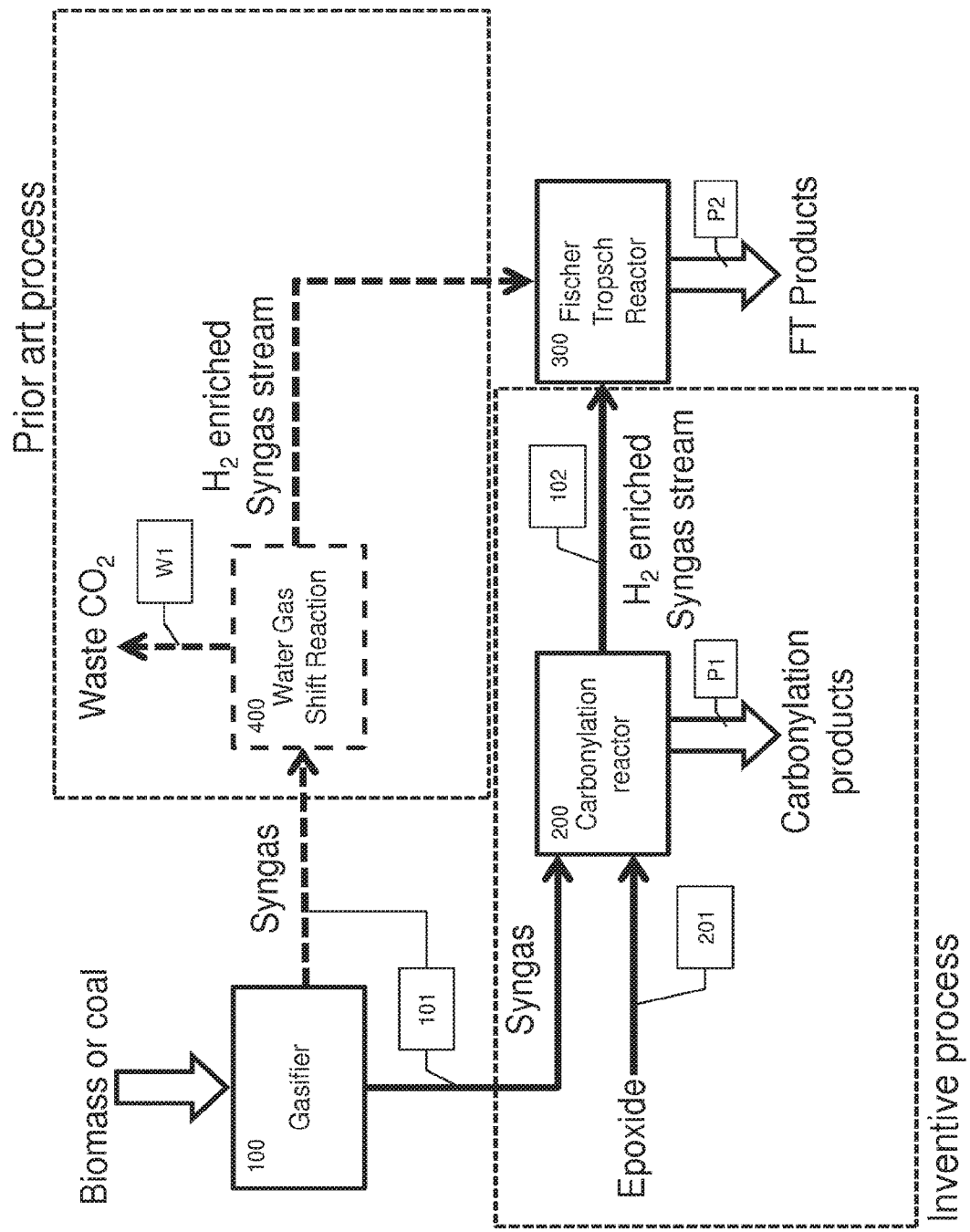
FIG. 1 shows a schematic of an integrated process according to the present invention.

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistr.* $5^{th}$ Edition, John Wiley & Sons. Inc., New York, 2001; Larock, *Comprehensive Organic Transformations*, VCH Publishers, Inc., New York, 1989; Carruthers, *Some Modern Methods of Organic Synthesis,* $3^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of enantiomers or diastereomers are provided.

Furthermore, certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example "isomers" include cis- and trans-isomers. E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of an enantiomer. In some embodiments the compound is made up of at least about 95%, 97%, 98%, 99%, 99.5%, 99.7%, 99.8%, or 99.9% by weight of an enantiomer. In some embodiments the enantiomeric excess of provided compounds is at least about 90%, 95%, 97%, 98%, 99%, 99.5%, 99.7%, 99.8%, or 99.9%. In some embodiments, enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel. E. L. *Stereochemistry of Carbon Compounds* (McGraw-Hill, N Y, 1962); Wilen. S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "glycidyl", as used herein, refers to an oxirane substituted with a hydroxyl methyl group or a derivative thereof. The term glycidyl as used herein is meant to include moieties having additional substitution on one or more of the carbon atoms of the oxirane ring or on the methylene group of the hydroxymethyl moiety, examples of such substitution may include, but are not limited to: alkyl groups, halogen atoms, aryl groups etc. The terms glycidyl ester, glycidyl acrylate, glydidyl ether etc. denote substitution at the oxygen atom of the above-mentioned hydroxymethyl group, i.e. that oxygen atom is bonded to an acyl group, an acrylate group, or an alkyl group respectively.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, but are not limited to, ethynyl, 2-propynyl (propargyl), 1-propynyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include cyclopropane, cyclobutane, cyclopentane, cyclohexane, bicyclo[2,2,1]heptane, norbornene, phenyl, cyclohexene, naphthalene, spiro[4.5] decane, The term "aryl" used alone or as part of a larger moiety as in "aralkyl". "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —N(R°)C(S)R°; —$(CH_2)_{0-4}N(R°)C(O)NR°_2$; —N(R°)C(S)NR°_2; —$(CH_2)_{0-4}N(R°)C(O)OR°$; —N(R°)N(R°)C(O)R°; —N(R°)N(R°)C(O)NR°_2; —N(R°)N(R°)C(O)OR°; —$(CH_2)_{0-4}C(O)R°$; —C(S)R°; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —OC(O)$(CH_2)_{0-4}SR°$, SC(S)SR°; —$(CH_2)_{0-4}SC(O)R°$; —$(CH_2)_{0-4}C(O)NR°_2$; —C(S)NR°_2; —C(S)SR°; —SC(S)SR°, —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R$; —$(CH_2)_{0-4}S(O)_2OR°$; —$(CH_2)_{0-4}S(O)_2R°$; —S(O)

NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —(CH$_2$)$_{0-2}$R•, -(haloR•), —(CH$_2$)$_{0-2}$OH, —(CH$_2$)$_{0-2}$OR•, —(CH$_2$)$_{0-2}$CH(OR•)$_2$; —O(haloR•), —CN, —N$_3$, —(CH$_2$)$_{0-2}$C(O)R•, —(CH$_2$)$_{0-2}$C(O)OH, —(CH$_2$)$_{0-2}$C(O)OR•, —(CH$_2$)$_{0-4}$C(O)N(R°)$_2$; —(CH$_2$)$_{0-2}$SR•, —(CH$_2$)$_{0-2}$SH, —(CH$_2$)$_{0-2}$NH$_2$, —(CH$_2$)$_{0-2}$NHR•, —(CH$_2$)$_{0-2}$NR•$_2$, —NO$_2$, —SiR•$_3$, —OSiR•$_3$, —C(O)SR•, —(C$_{1-4}$ straight or branched alkylene)C(O)OR•, or —SSR• wherein each R• is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$ wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

"Tetradentate" refers to ligands having four sites capable of coordinating to a single metal center.

As used herein, the term "about" preceding one or more numerical values means the numerical value ±5%.

DETAILED DESCRIPTION OF THE INVENTION

Among other things, the present invention provides integrated processes that enable simultaneous production of valuable chemicals or polymers while upgrading synthesis gas by increasing the hydrogen to carbon monoxide ratio. These inventive processes represent significant economic and environmental improvements versus prior art methods that utilize the water gas shift reaction for the production of H$_2$ and CO$_2$ from the reaction of CO and water. The integrated processes herein result in improved carbon efficiency for processes based on coal or biomass gasification or steam methane reforming, while producing valuable commodity chemicals instead of waste CO$_2$.

In a first aspect, the present invention provides integrated processes for the conversion of biomass, coal or natural gas to synthesize gas and commodity chemicals or polymers derived from epoxide carbonylation. In certain embodiments, such methods comprise the steps of:

a) in a first reaction zone, contacting syngas derived from gasification reactions with an epoxide in the presence of a carbonylation catalyst thereby consuming carbon monoxide from the syngas and producing an epoxide carbonylation product, b) recovering an upgraded gas stream from the first reaction zone wherein the upgraded gas stream has a higher hydrogen to carbon monoxide ratio than the starting syngas stream, c) in a second reaction zone, utilizing the upgraded gas stream to conduct a second chemical process requiring a hydrogen to carbon monoxide ratio higher than the ratio in the industrial gas stream utilized in step (a).

A schematic of a process according to this aspect of the invention is shown in FIG. 1. The process begins with a gasifier unit which converts biomass, coal or other carbonaceous feedstocks into a synthesis gas stream 101. Gas stream 101 is directed to carbonylation reactor 200 where it is brought into contact with an epoxide (fed to reactor 200 via stream 201). In reactor 200, the epoxide and carbon monoxide in the syngas stream react in the presence of a carbonylation catalyst to produce epoxide carbonylation products which are ultimately recovered via product stream P1. A hydrogen-enriched syngas stream 102 is recovered from reactor 200 and fed to reactor 300 where it is consumed as the feedstock for Fischer Tropsch synthesis yielding FT products via product stream P2. FIG. 1 also illustrates the prior art process wherein water gas shift reactor 400 is utilized in place of carbonylation reactor 200. In this case, CO in the synthesis gas stream 101 is converted to $CO_2$ and hydrogen in the usual fashion with $CO_2$ exiting via waste stream W1.

In another aspect, the present invention provides integrated processes for the conversion of syngas to hydrogen substantially free of carbon monoxide. In certain embodiments, such methods comprise the steps of:
  a) in a first reaction zone, contacting a syngas stream derived from methane steam reforming with an epoxide in the presence of a carbonylation catalyst thereby consuming carbon monoxide from the syngas and producing an epoxide carbonylation product,
  b) recovering an upgraded gas stream from the first reaction zone wherein the upgraded gas comprises hydrogen that is substantially free of carbon monoxide.

In a another aspect, the present invention provides integrated processes for the conversion of methane into hydrogen. In certain embodiments, such methods comprise the steps of:
  c) in a first reaction zone, contacting a syngas stream derived from methane steam reforming with an epoxide in the presence of a carbonylation catalyst thereby consuming carbon monoxide from the syngas and producing an epoxide carbonylation product,
  d) recovering an upgraded gas stream from the first reaction zone wherein the upgraded gas stream has a higher hydrogen to carbon monoxide ratio than the starting syngas stream, and
  e) in a second reaction zone, utilizing the upgraded gas stream to conduct a second chemical process requiring a hydrogen to carbon monoxide ratio higher than the ratio in the industrial gas stream utilized in step (a).

Figure 2:
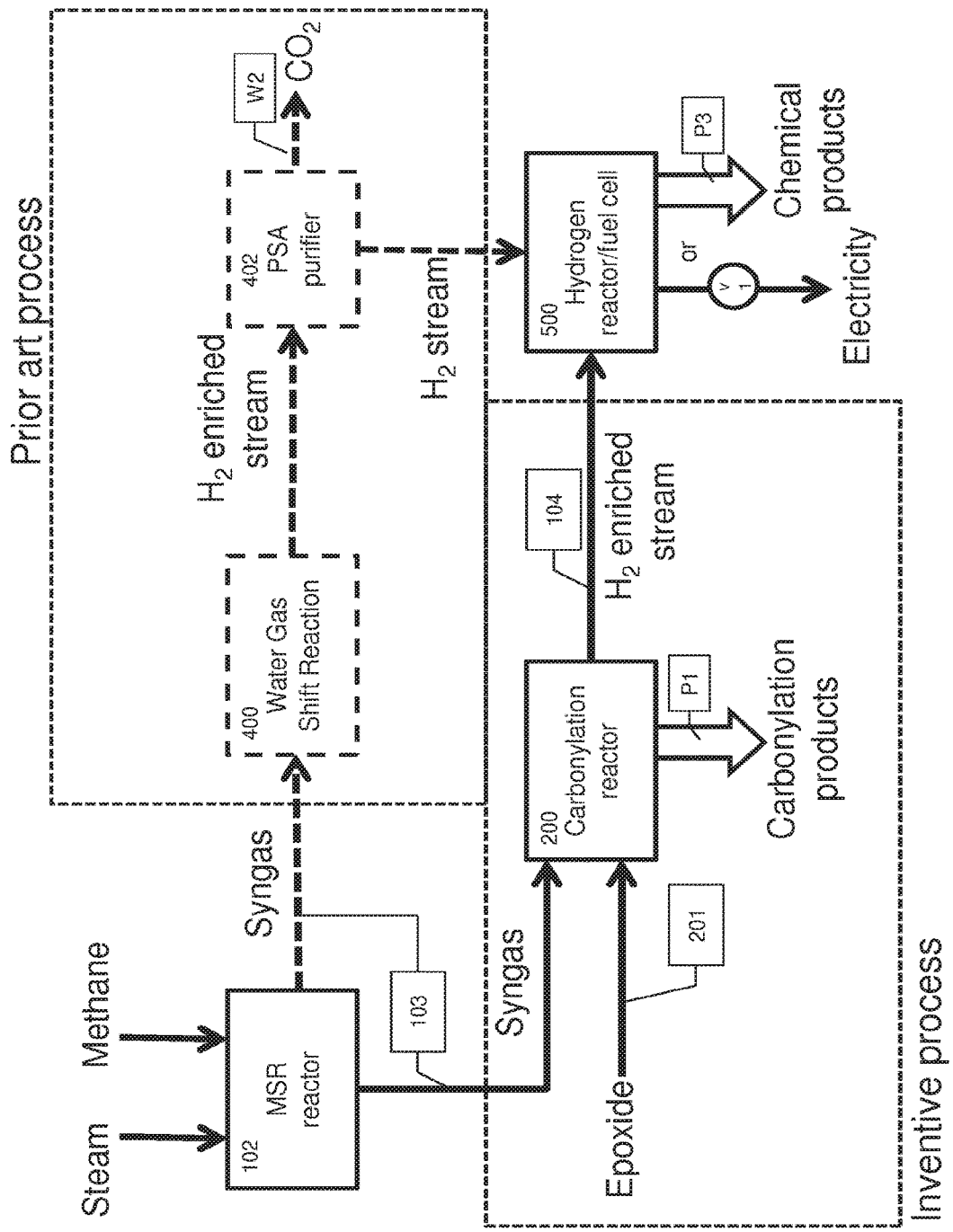
FIG. 2 shows a schematic of an integrated hydrogen production process according to the present invention.

FIG. 2 shows a schematic of one embodiment of such a process. With reference to that figure, a methane steam reforming reactor 102 which is fed with steam and methane to produce syngas stream 103. Gas stream 103 is fed to carbonylation reactor 200 along with epoxide (via stream 201). The epoxide and carbon monoxide react in the presence of a carbonylation catalyst in reactor 200 to produce product stream P1 containing carbonylation products and a hydrogen-enriched gas stream 104. The hydrogen enriched gas stream 104 can be used for known purposes requiring hydrogen or hydrogen-rich syngas. For example, as shown in FIG. 2, gas stream 104 can optionally be fed to a chemical reactor which consumes hydrogen to make chemical products (e.g. ammonia or hydrogenated products), or to a fuel cell to produce electricity collectively represented by reactor 500 and outputs P3 and V1. As described more fully below, in certain embodiments, carbonylation reactor 200 is operated under conditions such that essentially all of the carbon monoxide in syngas stream 103 is consumed, in which case stream 104 consists of substantially pure hydrogen. These embodiments have the attractive feature of eliminating the need for a pressure swing adsorption unit (e.g. PSA 402) or related purification stages.

In another aspect, the present invention provides an integrated process for the production of hydrogen and commodity chemicals derived from beta lactone carbonylation.

In certain embodiments, such methods comprise the steps of:
  a) in a first reaction zone, contacting syngas with a beta propiolactone in the presence of a carbonylation catalyst thereby consuming carbon monoxide from the syngas and producing a succinic anhydride product,
  b) recovering an upgraded gas stream from the first reaction zone wherein the upgraded gas stream has a higher hydrogen to carbon monoxide ratio than the starting syngas stream,
  c) in a second reaction zone, utilizing the upgraded gas stream to conduct a second chemical process requiring a hydrogen to carbon monoxide ratio higher than the ratio in the industrial gas stream utilized in step (a).

Figure 3:
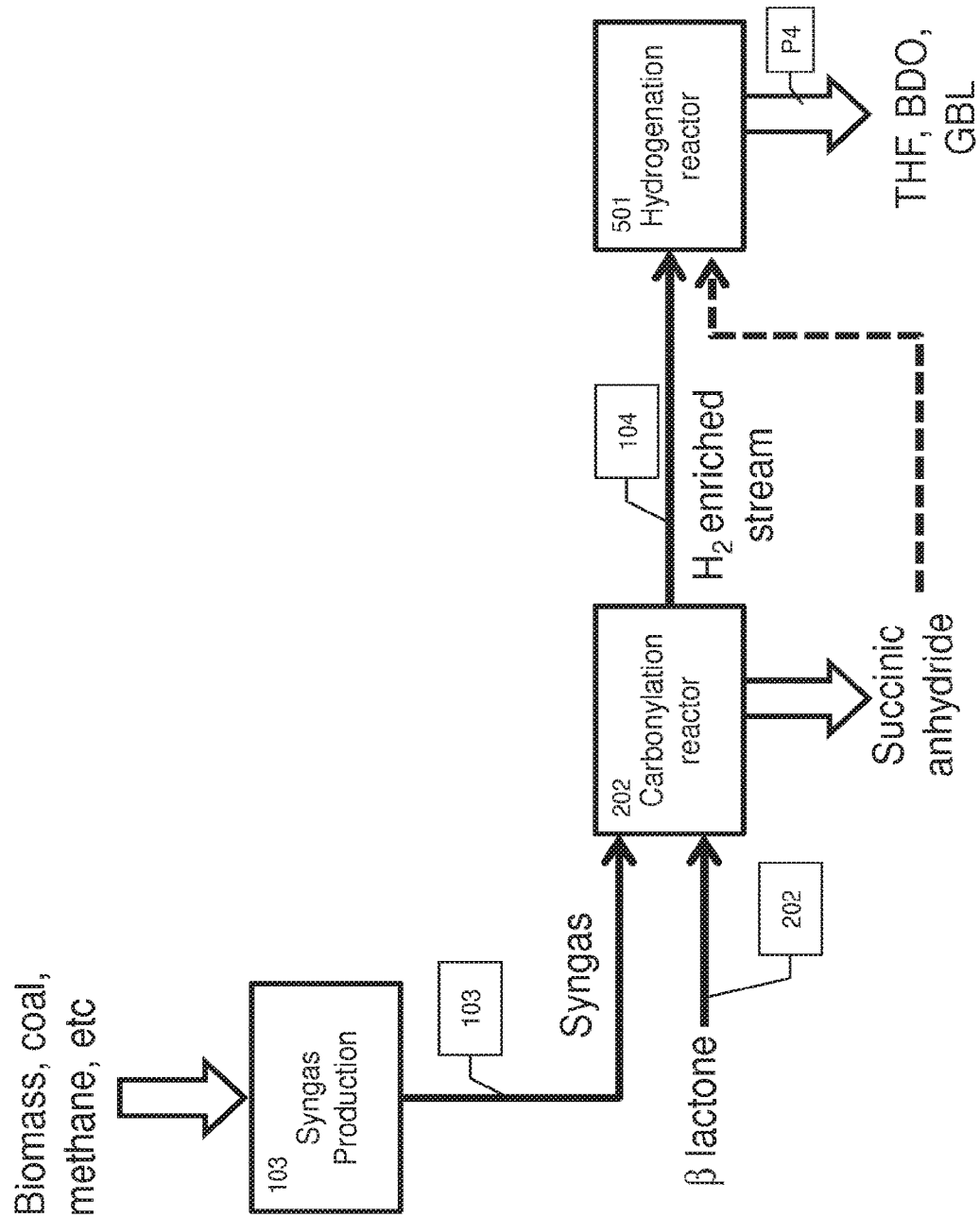
FIG. 3 shows a schematic of an alternate process according to the present invention.

FIG. 3 shows a schematic of a process according to this embodiment. As shown in FIG. 3, Syngas reactor 103 which is fed with appropriate inputs and produces syngas stream 103. Gas stream 103 is fed to carbonylation reactor 200 along with a beta lactone (via stream 202). The lactone and carbon monoxide react in the presence of a carbonylation catalyst in reactor 202 to produce a succinic anhydride product along with gas stream 104 which is enriched in hydrogen relative to stream 103. As shown, the succinic anhydride can optionally be fed to hydrogenation reactor 501 along with the hydrogen stream 104 and contacted under hydrogenation conditions to produce tetrahydrofuran (THF), 1,4 butanediol (BDO), or gamma butyrolactone (GBL).

Figure 4:
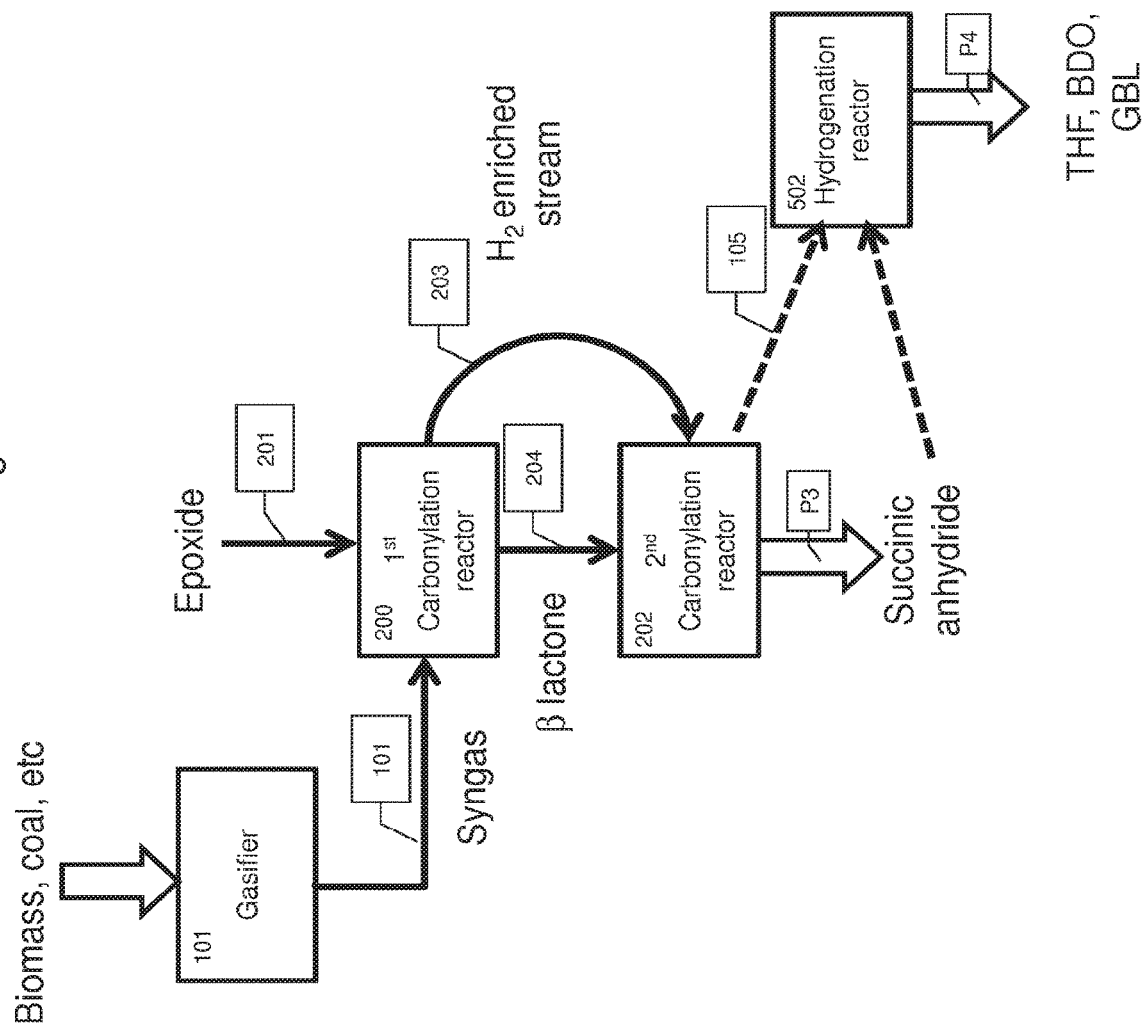
FIG. 4 shows a schematic of a process according to the present invention utilizing two carbonylation stages.

FIG. 4 shows a schematic of another embodiment of the invention where the syngas input is upgraded twice by utilizing two carbonylation stages. As shown in the figure, syngas is produced in gasifier 100 in the usual fashion, the output syngas stream 101 is directed to first carbonylation reactor 200 where it is contacted with an epoxide and a carbonylation catalyst to produce a beta lactone product and hydrogen enriched synthesis gas stream 103. Both the beta lactone and the gas stream 103 are directed to a $2^{nd}$ carbonylation reactor 202 where they are further reacted in the presence of a carbonylation catalyst (which may be the same or different from the catalyst in the $1^{st}$ carbonylation reactor) to produce a succinic anhydride product stream P3 along with a hydrogen stream 105. As shown these streams may optionally be combined in hydrogenation reactor 502 where the anhydride reacts with the hydrogen to produce a product stream P4 containing products selected from the group consisting of THF, BDO and GBL.

Having generally described the spirit of the methods encompassed by the present invention, the following sections provide additional details regarding the compositions of the feedstocks, process streams and products as well as appropriate process conditions and apparatus for practicing the inventive processes.

I) Syngas Production

The methods described herein do not place any specific restrictions on the method by which the syngas input is produced or on the specific composition of the syngas. The terms "synthesis gas" or "syngas" as used herein refer to any gaseous mixture of carbon monoxide and hydrogen. Such mixtures are typically produced from a carbonaceous feedstock. Syngas production methods include gasification of coal or biomass and steam reforming of methane or other gaseous or liquid hydrocarbons and similar processes.

In certain embodiments, the syngas stream fed to the carbonylation reactor in the methods described herein is characterized in that it has an $H_2$ to CO ratio between about 0.4:1 and about 1.5:1. Such a range is typical for syngas from solids gasification which tends to produce carbon rich syngas. In certain embodiments, the syngas stream fed to the carbonylation reactor is characterized in that it has an $H_2$ to CO ratio of 0.4:1, about 0.5:1, about 0.6:1, about 0.7:1, about 0.8:1, about 1:1, about 1.2:1, about 1.4:1, or about 1.5:1. In certain embodiments, the syngas stream fed to the carbonylation reactor is characterized in that it has an $H_2$ to CO ratio less than about 1.6:1, less than about 1.5:1, less than about 1.3:1, less than about 1.2:1, less than about 1.1:1, less than about 1:1, less than about 0.8:1, less than about 0.7:1, or less than about 0.6:1.

In certain embodiments, the syngas stream fed to the carbonylation reactor in the methods described herein is characterized in that it has an $H_2$ to CO ratio between about 1.5:1 and about 3:1. Such a range is typical for steam reforming processes utilizing methane or other light aliphatic feedstocks. In certain embodiments, the syngas stream fed to the carbonylation reactor is characterized in that it has an $H_2$ to CO ratio of 1.5:1, about 1.6:1, about 1.8:1, about 2:1, about 2.4:1, about 2.8:1, or about 3:1. In certain embodiments, the syngas stream fed to the carbonylation reactor is characterized in that it has an $H_2$ to CO ratio than about 3:1, less than about 2.8:1, less than about 2.5:1, less than about 2.2:1, or less than about 2:1.

Syngas typically contains varying amounts of $CO_2$. In many catalytic processes the $CO_2$ must be removed prior to using the gas. This issue is more acute in processes relying on biomass gasification since the high oxygen content of biobased feedstocks typically produces syngas with high $CO_2$ content (often 20% or more). The presence of $CO_2$ not only potentially compromises downstream catalytic processes, but its presence in the syngas stream means that any process steps (e.g. compression or desulfurization) performed prior to removal of the $CO_2$ are less efficient since the $CO_2$ dilutes the stream and therefore requires higher processing capacity. Unexpectedly, the applicants have discovered that epoxide carbonylation reactions promoted by certain classes of catalysts described below are tolerant of high levels of $CO_2$ in the syngas stream.

Therefore, in certain embodiments, the syngas stream fed to the carbonylation reactor in the methods described herein is characterized in that it contains $CO_2$. In certain embodiments, the syngas stream contains between about 1 mole percent and about 30 mole percent $CO_2$. In certain embodiments, the syngas stream contains between about 1 mole percent and about 5 mole percent $CO_2$, between about 5 mole percent and about 10 mole percent $CO_2$, between about 10 mole percent and about 20 mole percent $CO_2$, or between about 20 mole percent and about 40 mole percent $CO_2$.

Nevertheless, in some circumstances, it may be desirable to provide a syngas stream which contains little or no $CO_2$ to the carbonylation step. Therefore, in certain embodiments, the syngas stream fed to the carbonylation reactor in the methods described herein is characterized in that it contains little or no $CO_2$. In certain embodiments, the syngas stream fed to the carbonylation reactor contains less than about 2000 ppm, less than about 1000 ppm, less than about 500 ppm, less than about 200 ppm, less than about 100 ppm, less than about 50 ppm, less than about 25 ppm, or less than about 10 ppm $CO_2$.

Without being bound by theory or thereby limiting the scope of the claimed invention, it is believed that the presence of sulfur compounds in the syngas stream is deleterious to the epoxide carbonylation reactions described herein. Therefore in certain embodiments, the syngas stream fed to the carbonylation reactor is substantially free of sulfur. In certain embodiments, the syngas stream fed to the carbonylation reactor contains less than about 500 ppm, less than 200 ppm, less than about 100 ppm, less than about 50 ppm, less than about 40 ppm, or less than about 25 ppm sulfur. In certain embodiments, the syngas stream fed to the carbonylation reactor contains less than about 10 ppm, less than about 5 ppm, less than about 2 ppm, less than about 1 ppm, or less than about 0.5 ppm sulfur. In certain embodiments, the syngas stream fed to the carbonylation reactor contains less than about 0.2 ppm, less than about 0.1 ppm, less than about 0.05 ppm, less than about 0.01 ppm, or less than about 0.001 ppm sulfur.

It will be appreciated by the skilled artisan that production of syngas is a mature technology which is capable of operating with a diverse array of feedstocks and that numerous process conditions and catalysts for production of syngas are known in the art. Likewise apparatus and methods for the handling and purification of syngas are well known. As such, the selection of appropriate feedstocks and process conditions to produce syngas suitable for practice of the inventive methods described herein will be apparent to the skilled artisan based on the teachings and disclosure herein. The exact choice of feedstocks and processing methods is likely to depend on the local availability of materials and prevailing economic conditions.

II) Carbonylation Reaction Conditions

As described above and in the classes and subclasses herein, the inventive methods comprise a step of contacting the syngas stream with a carbonylation catalyst in the presence of an epoxide or a beta lactone. Catalysts, conditions and processes for these carbonylation reactions are well known in the art and can be employed in the methods described herein.

For embodiments where the syngas is reacted with an epoxide, no particular constraints are placed on the identity of the epoxide. Any epoxide or mixture of epoxides may be used, though as a general principle those epoxides lacking other reactive functional groups (for example protic functional groups) are less desirable since there is an increased likelihood for side reactions with use of such substrates. Also, given the large scale on which syngas production is typically practiced, there is a strong preference to utilize epoxides that are available in bulk as commodity chemicals.

In certain embodiments where the methods entail epoxide carbonylation reactions, the epoxide is selected from the group consisting of: ethylene oxide, propylene oxide, butylene oxide, 1-hexene oxide, epichlorohydrin, and esters or ethers of glycidol. In certain embodiments, the epoxide is selected from the group consisting of ethylene oxide and propylene oxide. In certain embodiments the epoxide is ethylene oxide. In certain embodiments the epoxide is propylene oxide.

The catalytic insertion of CO into epoxides is known to yield several possible products the identity of which is influenced by the particular catalyst utilized and the reaction conditions employed. In certain embodiments of the present invention comprising a step of carbonylating an epoxide, the product of the carbonylation is selected from the group consisting of: a beta lactone, a 3-hydroxy propionic acid, a succinic anhydride (via double carbonylation) and polyesters comprising the alternating copolymer of the epoxide and CO.

In certain embodiments, carbonylation results in the formation of a beta lactone by the general reaction:

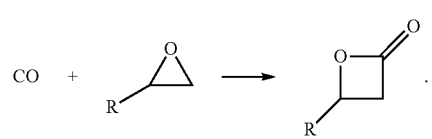

Examples include:
propylene oxide+CO→beta butyrolactone

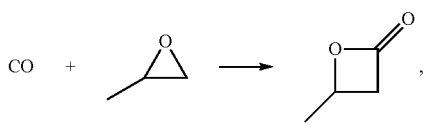

and
ethylene oxide+CO→beta propiolactone

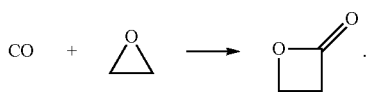

Suitable catalysts and reaction conditions for effecting this reaction are disclosed in published PCT applications: WO2003/050154, WO2004/089923, WO2012/158573, WO2010/118128, WO2013/063191, and WO2014/008232; in U.S. Pat. Nos. 5,359,081 and 5,310,948 and in the publication "Synthesis of beta-Lactones" J. AM. CHEM. SOC., vol. 124, 2002, pages 1174-1175. The entirety of each of the preceding references is hereby incorporated herein by reference.

In certain embodiments, carbonylation results in the formation of a polyester by the general reaction:

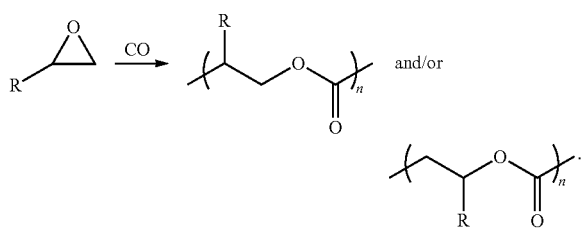

Examples include propylene oxide+CO→poly(3-hydroxybutyrate)

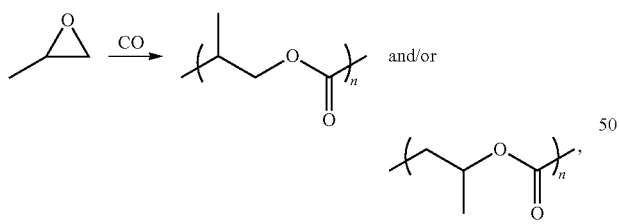

and
ethylene oxide+CO→poly propiolactone

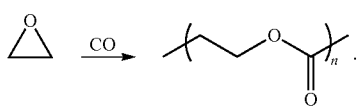

In certain embodiments where methods of the present invention include a step of carbonylative polymerization, the methods utilize catalysts and/or process conditions disclosed in published PCT applications WO2003/074585A1, WO2011/063309, or WO2014004858 each of which is incorporated herein by reference in its entirety.

In certain embodiments, epoxide carbonylation results in the formation of a succinic anhydride by insertion of two molecules of CO. Such processes conform to the general reaction scheme:

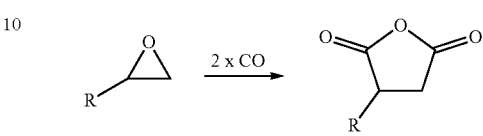

Examples include propylene oxide+CO→methylsuccinic anhydride

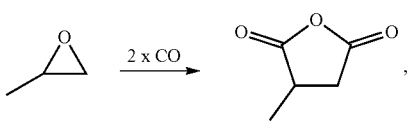

and
ethylene oxide+CO→succinic anhydride

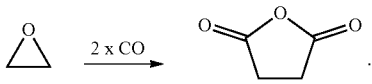

In certain embodiments, where methods of the present invention include double carbonylation of epoxides, the methods utilize catalysts and/or process conditions disclosed in published PCT applications WO2012/030619 and WO2013/122905, and U.S. Pat. No. 8,481,756, each of which is incorporated by reference herein in its entirety.

As described above, certain embodiments of the present invention comprise a step of contacting a syngas stream with a beta lactone in the presence of a carbonylation catalyst to yield a succinic anhydride derivative along with a hydrogen-enriched syngas stream. Such processes conform to the general reaction scheme:

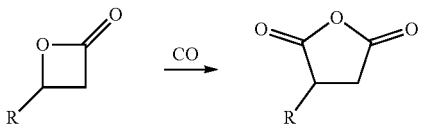

The catalysts and/or process conditions disclosed in published PCT applications WO2012/030619 and WO2013/122905, and U.S. Pat. No. 8,481,756, can be utilized to perform such steps.

In certain embodiments, carbonylation catalysts utilized in the present methods comprise metal carbonyl complexes. In certain embodiments, the catalysts comprise metal carbonyl complexes in combination with one or more other components such as amines, nitrogen-containing heterocycles, Lewis acids, or metal complexes.

Typically, where a carbonylation catalyst utilized in methods herein comprises a metal carbonyl, a single metal carbonyl compound is provided, but in certain embodiments mixtures of two or more metal carbonyl compounds are provided. (Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more additional metal carbonyl compounds.) Preferably, the provided metal carbonyl compound is capable of ring-opening an epoxide and facilitating the insertion of CO into the resulting metal carbon bond. Metal carbonyl compounds with this reactivity are well known in the art and are used for laboratory experimentation as well as in industrial processes such as hydroformylation. Additional description of suitable metal carbonyl compounds is provided in Appendix I at the end of this specification.

As mentioned above, carbonylation catalysts useful for practicing methods of the present invention may include one or more additional components in combination with a metal carbonyl compound. In certain embodiments, such additional components comprise organic bases such as optionally substituted amines, guanidines, or amidines and the like. In certain embodiments, such additional components comprise heterocycles such as optionally substituted pyridines, pyrimidines, imidazoles, and the like. In certain embodiments, such additional components comprise neutral Lewis acids such as boranes, aluminum alkyls, $TiCl_4$, $BF_3$, and the like. In certain embodiments, such additional components comprise cationic Lewis acids. Additional description of suitable cationic Lewis acids is provided in Appendix 11 at the end of this specification.

In certain embodiments, the carbonylation catalysts employed in methods of the present invention comprise heterogeneous carbonylation catalysts. In certain embodiments, such heterogeneous catalysts comprise supported metal carbonyl compounds. In certain embodiments, carbonylation catalysts and processes disclosed in WO 2013/063191 may be adapted for use in methods of the present invention.

The methods of the present invention provide no specific limitations on the reaction conditions utilized in the carbonylation step. For practical application on industrial scale, the carbonylation reaction will typically be performed in a continuous or semi-continuous format. Where the carbonylation reaction is performed in a continuous fashion, it may be conducted in any suitable reactor format, such as plug flow reactors (PFRs), continuous stirred-tank reactors (CSTRs) or any hybrid or combination of these. Though the carbonylation stage of the methods herein is often described as a single step, it may in fact occur in multiple steps such as within a series of continuous stirred tank reactors or a plug flow reactor fed by one or more CSTRs. Continuous operation requires additional processing steps and suitable apparatus to continuously feed reactants, catalysts, solvents and the like as well as provision to continuously withdraw carbonylation products, recycle the catalyst and solvents, purge impurities, and the like. A detailed description of such processes and apparatus is outside the scope of this disclosure since the requisite knowledge is readily available to the skilled artisan. In certain embodiments, the continuous carbonylation processes described in published PCT applications WO 2010/118128 WO 2012/030619 WO 2013/063191 WO 2013/122905 and WO 2014008232 are suitable for practicing certain embodiments of the methods described herein.

The syngas will typically be fed to the carbonylation reactor at a superatmospheric pressure. No particular limits are placed on the pressure utilized—as with similar processes the chosen operating pressure will require balance of the reaction rate and selectivity at a given pressure with the cost of the equipment required to operate at that pressure. In certain embodiments, the syngas is provided to the carbonylation reactor at a pressure from about 50 psi to about 5,000 psi. If the source of the synthesis gas provides a gas stream at a pressure lower than the desired pressure in the carbonylation step, then the methods will include an additional step of pressurizing the syngas stream prior to contacting it with the epoxide or beta lactone. In certain embodiments, the carbonylation reactor is integrated with a syngas production source that outputs a pressurized source of syngas and the carbonylation reactor is run at a pressure substantially the same as the output from the syngas source.

In certain embodiments, the syngas is provided to the carbonylation reactor at a pressure sufficient to afford a carbon monoxide partial pressure within the reactor from about 0.5 atmospheres to about 350 atmospheres. In certain embodiments, the carbon monoxide partial pressure ranges from about 5 to about 100 atmospheres. In certain embodiments, the carbon monoxide partial pressure ranges from about 10 to about 50 atmospheres, from about 5 to about 20 atmospheres, from about 1 to about 10 atmospheres, or from about 25 to about 50 atmospheres. In some embodiments, carbon monoxide partial pressure within the carbonylation reactor ranges from about 0.5 atmospheres to about 10 atmospheres. In some embodiments, a carbon monoxide partial pressure within the carbonylation reactor ranges from about 0.5 to about 50, from about 1 to about 10, from about 1 to about 50, from about 1 to about 100, from about 10 to about 50, from about 10 to about 100, from about 50 to about 100, from about 50 to about 200, from about 100 to about 200, from about 100 to about 250, from about 200 to about 300, or from about 200 to about 500 atmospheres. In some embodiments, a carbon monoxide partial pressure within the carbonylation reactor is about 10 atmospheres. In some embodiments, a carbon monoxide partial pressure within the carbonylation reactor is about 10, about 20, about 30, about 40, about 50, about 100, about 150, or about 200 atmospheres.

In certain embodiment, the step of contacting the syngas stream with epoxide or beta lactone in the presence of a carbonylation catalyst is performed under conditions such that the hydrogen-to-carbon monoxide ratio in the upgraded syngas stream exiting the reactor is maintained within a specific range. In certain embodiments, the desired range is dependent on the identity of the downstream process in which the upgraded gas stream is to be used. For integrated carbonylation-Fischer Tropsch processes, it is desirable to maintain the $H_2$ to CO ratio of the upgraded syngas stream around 2:1. For integrated carbonylation-hydrogenation processes, it is desirable to maintain the $H_2$ to CO ratio at a high level, or even to consume substantially all of the CO in the syngas feed stream such that the upgraded stream contains little or no CO. Therefore, in certain embodiments methods of the present invention are characterized in that the upgraded syngas stream obtained from the carbonylation reactor has an $H_2$ to CO ratio above about 2:1. In certain embodiments, the upgraded syngas stream obtained from the carbonylation reactor has an $H_2$ to CO ratio above about 2.1:1, above about 2.2:1, above about 2.3:1, above about 2.4:1, above about 2.1:1, above about 2.1:1, above about 2.1:1, above about 2.1:1, above about 2.5:1, above about 2.8:1, above about 3:1, above about 3.5:1, above about 4:1, above about 5:1, or above about 10:1. In certain embodiments, the upgraded syngas stream obtained from the carbonylation reactor has an $H_2$ to CO ratio above about 2.1:1, above about 10:1, above about 20:1, above about 50:1, above about 100:1, above about 200:1, above about 500:1, or above about 1000:1.

In certain embodiments methods of the present invention are characterized in that the upgraded syngas stream obtained from the carbonylation reactor has an $H_2$ to CO ratio of about 2:1. In certain embodiments, the upgraded syngas stream obtained from the carbonylation reactor has an $H_2$ to CO ratio of about 2.1:1, about 2.2:1, about 2.5:1, about 3:1, about 4:1, about 5:1, or about 10:1.

In certain embodiments methods of the present invention are characterized in that the upgraded syngas stream obtained from the carbonylation reactor is essentially free of CO. In certain embodiments, the upgraded syngas stream obtained from the carbonylation reactor contains less than 2%, less than 1%, less than 0.5%, less than 0.2%, or less than 0.1% CO. In certain embodiments, the upgraded syngas stream obtained from the carbonylation reactor contains less than 500 ppm, less than 400 ppm, less than 200 ppm, less than 100 ppm, less than 50 ppm, less than 25 ppm, less than 10 ppm, less than 5 ppm, or less than 1 ppm CO.

III) Utilization of the Upgraded Syngas Stream

The upgraded syngas stream from the carbonylation reactor may be recovered and handled by any suitable means. Typically the upgraded syngas stream will exit the carbonylation reactor via a gas vent, a back-pressure regulator or an outlet port which may include provision for liquids separation, recompression, scrubbing, drying, chilling or heating, and the like as is typically performed in industry. In certain embodiments, the carbonylation reactor is operated at a higher pressure than the downstream process fed with the upgraded syngas stream that exits the carbonylation reactor. This has the advantage of not requiring recompression of the upgraded syngas stream. Nonetheless, this is not always possible if the downstream process is one that requires high hydrogen partial pressures. In this case, the methods of the present invention will include a step of compressing the upgraded syngas stream prior to utilizing it in next process.

In certain embodiments, the upgraded syngas stream exiting the carbonylation reactor will contain impurities that must be removed prior to utilization of the upgraded stream. For example, if the stream contains carbon dioxide and the downstream process is not tolerant of $CO_2$, then the methods necessarily require an intermediate step to scrub $CO_2$ from the upgraded stream. Such methods are well known in the art and may include membrane separation, pressure swing adsorption, chemical adsorption, cryotreatment and the like. In certain embodiments, volatile residues from the carbonylation reactor may be present in the upgraded syngas stream. Such residues may include solvent, unreacted epoxide, carbonylation side products such as acetaldehyde, volatile metal carbonyl residues and the like. In certain embodiments, the upgraded syngas stream is treated to remove such impurities prior to utilization of the stream in a downstream process. In certain embodiments where the downstream process is tolerant of such residues, it may be preferable to leave the impurities in the upgraded syngas stream and purge them at a later stage in the process.

As described above a feature of some methods of the present invention is the use of the upgraded syngas stream in a downstream process. Preferably, the carbonylation stage of the methods increases the $H_2$:CO ratio in the stream to a range that is desirable for the downstream process.

In certain embodiments, the downstream process comprises Fischer-Tropsch (FT) synthesis. FT technology is a mature field and appropriate operating conditions, apparatus, catalysts and product isolation techniques for FT processes are well known in the art. The skilled artisan utilizing the wealth of knowledge available in the FT field, together with the teachings herein, will readily apprehend suitable configurations for the FT step described in methods herein. An overview of FT technology is provided in Advance Catalysis. Volume 186, pp 3-12, the entirety of which is incorporated herein by reference.

In certain embodiments the downstream process in which the upgraded syngas stream is utilized is an FT gas-to-liquid process for the production of fuels and/or chemicals such as olefins and/or alcohols. In certain embodiments, the downstream process in which the upgraded syngas stream is utilized is a Low Temperature FT synthesis (LTFT). In certain embodiments, the downstream process in which the upgraded syngas stream is utilized is a High Temperature FT synthesis (HTFT). The Fischer Tropsch reactor in which the upgraded syngas stream is utilized may be of any known configuration. Suitable configurations include multitubular fixed bed reactors, entrained flow reactors, slurry reactors, bubble reactors, fluidized bed reactors, and riser reactors. Likewise, any known FT catalyst system may be employed in the present methods. Suitable catalysts include, but are not limited to: cobalt, iron, ruthenium, nickel, and any combination of two or more of these. The FT catalysts may include additional components as are known in the art including alkaki metals, copper, manganese, lanthanide metals or compounds, actinide metals or compounds, alumina, zirconia, and the like.

In certain embodiments the downstream process in which the upgraded syngas stream is utilized is a process for the production of methane. Suitable catalysts and conditions for methane synthesis from syngas are known in the art and the skilled artisan utilizing the teachings herein with the known art will apprehend suitable conditions, apparatus and catalyst systems to effect the conversion of the upgraded syngas stream to methane.

In certain embodiments the downstream process in which the upgraded syngas stream is utilized is a process for the production of methanol. Suitable catalysts and conditions for methanol synthesis from syngas are known in the art and the skilled artisan utilizing the teachings herein with the known art will apprehend suitable conditions, apparatus and catalyst systems to effect the conversion of the upgraded syngas stream to methanol.

In certain embodiments the downstream process in which the upgraded syngas stream is utilized is a process for the production of dimethyl ether. Suitable catalysts and conditions for methanol synthesis from syngas are known in the art and the skilled artisan utilizing the teachings herein with the known art will apprehend suitable conditions, apparatus and catalyst systems to effect the conversion of the upgraded syngas stream to methanol.

In other embodiments, the integrated upgraded syngas stream is utilized as a fuel. For example, the upgraded syngas stream can be fed to a fuel cell, combusted in a turbine or boiler, or used to fuel an internal combustion engine. Therefore, depending on the process utilized, processes of the present invention may provide an output comprising steam, thermal energy, electrical energy, or mechanical energy. Due to the higher $H_2$ to CO ratio in the upgraded gas stream, the upgraded stream may have a higher energy content than the starting syngas stream (it will be appreciated that whether or not this is the case will depend on the amount of other gasses such as $CO_2$ that may also be present in the streams).

IV) Integrated Production of FT Products and EO Carbonylation Products

As described above, in certain embodiments, the present invention encompasses methods for the integrated production of chemicals from syngas derived from gasification.

In certain embodiments, such processes produce as final outputs, beta propiolactone or polypropiolactone (or derivatives of these such as acrylic acid, acrylate esters or superabsorbent polymers) by ethylene oxide carbonylation and FT products such as liquid fuels and related chemicals.

In certain embodiments, methods of the present invention comprise the steps of:
a) gasifying a carbonaceous solid to provide a syngas stream having an $H_2$ to CO ratio in the range from about 0.4:1 to about 1.2:1;
b) feeding this syngas stream to an epoxide carbonylation reactor where the syngas stream is contacted with ethylene oxide in the presence of a carbonylation catalyst to deplete the syngas of at least a portion of its CO content and provide a carbonylation product selected from the group consisting of: beta propiolactone, and polypropiolactone;
c) recovering an upgraded syngas stream from the carbonylation reactor characterized in that the upgraded stream has a higher $H_2$ to CO ratio than the syngas stream provided by step (a); and
d) feeding the upgraded syngas stream to a Fischer Tropsch reactor to produce a product selected from the group consisting of: liquid fuels, oils, waxes, olefins, alcohols, and any combination of two or more of these.

In certain embodiments, step (a) of the method above comprises coal gasification. In certain embodiments, such methods are characterized in that the syngas stream in step (a) has an $H_2$ to CO ratio of from about 0.6:1 to about 0.8:1. In certain embodiments, such methods are characterized in that the syngas stream in step (a) has an $H_2$ to CO ratio of about 0.7:1.

In certain embodiments, step (a) of the method above comprises biomass gasification. In certain embodiments, the biomass is selected from the group consisting of: corn stover, sugar cane bagasse, switch grass, municipal solid waste, and wood waste. In certain embodiments, such methods are characterized in that the syngas stream in step (a) has an H2 to CO ratio of from about 0.4:1 to about 0.8:1. In certain embodiments, such methods are characterized in that the syngas stream in step (a) has an $H_2$ to CO ratio of about 0.6:1. In certain embodiments, such methods are characterized in that the syngas stream in step (a) has an $H_2$ to CO ratio of about 0.5:1.

In certain embodiments, the method above comprises an additional step of compressing the syngas stream prior to feeding it to the carbonylation reactor. In certain embodiments, the method above comprises an additional step of removing nitrogenous and sulfurous compounds from the syngas stream prior to feeding it to the carbonylation reactor. In certain embodiments, the method above comprises an additional step of drying the syngas stream prior to feeding it to the carbonylation reactor. In certain embodiments, the method above comprises an additional step of removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, the product of step (b) of the method above comprises beta propiolactone and the method comprises an additional step of converting the beta propiolactone to acrylic acid, or acrylate esters.

In certain embodiments, the product of step (b) of the method above comprises beta propiolactone and the method comprises an additional step of converting the beta propiolactone to succinic anhydride. In certain embodiments such methods comprise an additional step of converting the succinic anhydride to a product selected from the group consisting of: succinic acid, 1,4 butanediol, tetrahydrofuran, gamma butyrolactone, or any combination of two or more of these.

In certain embodiments where the method above comprises an additional step of converting beta propiolactone to succinic anhydride, the conversion is conducted in a second carbonylation reactor. In certain embodiments, the second carbonylation reactor is also fed with the syngas stream produced in step (a) where it is contacted with the beta propiolactone in the presence of a carbonylation catalyst to deplete the syngas of at least a portion of its CO content and provide succinic anhydride as a second carbonylation product. In certain embodiments, a second upgraded syngas stream, characterized in that it has a higher $H_2$ to CO ratio that the syngas stream produced in step (a) is recovered from the second carbonylation reactor. In certain embodiments, the first and second upgraded syngas streams are combined and utilized in step (d).

In certain embodiments where the method above comprises an additional step of converting beta propiolactone to succinic anhydride, the conversion is conducted in a second carbonylation reactor which is fed with the upgraded syngas stream produced in step (b) where it is contacted with the beta propiolactone in the presence of a carbonylation catalyst to further deplete the upgraded syngas stream of its CO thereby providing a twice-upgraded syngas stream having a higher $H_2$ to CO ratio than the upgraded syngas stream from step (c). In certain embodiments, the method comprises an additional step of recovering the twice upgraded syngas stream from the second carbonylation reactor and feeding it to the FT reactor in step (d).

In certain embodiments, the product of step (b) of the method above comprises polypropiolactone and the method comprises an additional step of pyrolyzing the polypropiolactone to produce acrylic acid.

In certain embodiments, the carbonylation catalyst in step (b) of the method above comprises a metal carbonyl compound. In certain embodiments, the metal carbonyl compound is selected from any of those described in Appendix I. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described in Appendix II. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound from Appendix I and a metal complex from Appendix II.

In certain embodiments, step (c) in the method above is characterized in that the upgraded syngas stream recovered has an $H_2$ to CO ratio between about 1.2:1 and about 3:1. In certain embodiments, the upgraded syngas stream recovered has an H, to CO ratio between about 1.6:1 and about 2.8:1, between about 1.8:1 and about 2.6:1, between about 1.8:1 and about 2.2:1, or between about 1.9:1 and about 2.1:1. In certain embodiments, the upgraded syngas stream recovered has an $H_2$ to CO ratio of about 2:1.

In certain embodiments, the method above is characterized in that the reaction pressure in the carbonylation reactor is higher than the reaction pressure in the FT reactor. In certain embodiments, the upgraded syngas stream is fed to the FT reactor without an intermediate compression step. In certain embodiments, the upgraded syngas stream exits the carbonylation reactor via a backpressure regulator and is fed directly to the FT reactor.

In certain embodiments, the method above is characterized in that the upgraded syngas stream is treated to remove one or more components prior to feeding the stream to the FT reactor. In certain embodiments, the upgraded syngas stream is treated to remove residual solvent prior to feeding the stream to the FT reactor. In certain embodiments, the upgraded syngas stream is treated to remove residual epoxide prior to feeding the stream to the FT reactor. In certain embodiments, the upgraded syngas stream is treated to remove carbon dioxide prior to feeding the stream to the FT reactor.

In certain embodiments, the method above is characterized in that the FT reactor in step (d) is a Low Temperature FT synthesis (LTFT) reactor. In certain embodiments, the downstream process in which the upgraded syngas stream is utilized is a High Temperature FT synthesis (HTFT) reactor.

In certain embodiments, the method above is characterized in that the overall process has a carbon efficiency greater than 50%. That is, at least 50% of the carbon atoms fed to the gasification reactor are contained in the combined products from the EO carbonylation reactor and the FT reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

In certain embodiments, the method above is characterized in that the FT process in step (d) is fed with syngas from the gasification process in step (a) without utilizing the water gas shift reaction to increase its $H_2$ to CO ratio.

V) Integrated Production of EO Carbonylation Products and Purification of Hydrogen As described above, in certain embodiments, the present invention encompasses methods for the integrated production of chemicals and purified hydrogen.

In certain embodiments, such processes produce as final outputs, beta propiolactone or polypropiolactone (or derivatives of these such as acrylic acid, acrylate esters or superabsorbent polymers) by ethylene oxide carbonylation and hydrogen or products of hydrogen such as electrical energy, ammonia, or hydrogenated chemicals.

In certain embodiments, methods of the present invention comprise the steps of:
  a) producing a syngas stream by gasification or reforming technologies;
  b) feeding this syngas stream to an epoxide carbonylation reactor where the syngas stream is contacted with ethylene oxide in the presence of a carbonylation catalyst to deplete the syngas of at least a portion of its CO content and provide a carbonylation product selected from the group consisting of: beta propiolactone, and polypropiolactone; and
  c) recovering a hydrogen stream from the carbonylation reactor characterized in that the hydrogen stream has a higher $H_2$ to CO ratio than the syngas stream provided by step (a).

In certain embodiments, step (a) of the method above comprises steam methane reforming. In certain embodiments, such methods are characterized in that the syngas stream in step (a) has an $H_2$ to CO ratio of from about 2.8:1 to about 3.2:1. In certain embodiments, such methods are characterized in that the syngas stream in step (a) has an $H_2$ to CO ratio of about 3:1.

In certain embodiments, the method above comprises an additional step of compressing the syngas stream prior to feeding it to the carbonylation reactor. In certain embodiments, the method above comprises an additional step of removing sulfurous compounds from the syngas stream prior to feeding it to the carbonylation reactor. In certain embodiments, the method above comprises an additional step of drying the syngas stream prior to feeding it to the carbonylation reactor. In certain embodiments, the method above comprises an additional step of removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, the product of step (b) of the method above comprises beta propiolactone and the method comprises an additional step of converting the beta propiolactone to acrylic acid, or acrylate esters.

In certain embodiments, the product of step (b) of the method above comprises polypropiolactone and the method comprises an additional step of pyrolyzing the polypropiolactone to produce acrylic acid.

In certain embodiments, the carbonylation catalyst in step (b) of the method above comprises a metal carbonyl compound. In certain embodiments, the metal carbonyl compound is selected from any of those described in Appendix I. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described in Appendix II. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound from Appendix I and a metal complex from Appendix II.

In certain embodiments, the method above is characterized in that the hydrogen stream recovered in step (c) has an $H_2$ to CO ratio between about 4:1 and about 1,000:1. In certain embodiments, the upgraded syngas stream recovered has an $H_2$ to CO ratio between about 5:1 and about 10:1, between about 10:1 and about 50:1, between about 50:1 and about 100:1, or between about 100:1 and about 1000:1. In certain embodiments, the hydrogen stream contains essentially no CO.

In certain embodiments, the method above is characterized in that the hydrogen stream is treated to remove one or more components prior to use. In certain embodiments, the hydrogen stream is treated to remove residual solvent prior to use. In certain embodiments, the hydrogen stream is treated to remove residual epoxide prior to use. In certain embodiments, the hydrogen stream is treated to remove carbon dioxide prior to use.

In certain embodiments, the method above is characterized in that the hydrogen stream is utilized on site for a process selected from: ammonia synthesis, powering a fuel cell, hydrogenation, and any combination of two or more of these. In certain embodiments, the hydrogen is compressed and distributed for use elsewhere.

In certain embodiments, the method above is characterized in that the overall process has a carbon efficiency greater than 50%. That is, at least 50% of the carbon atoms fed to the steam reforming reactor are contained in products from the EO carbonylation reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

VI) Integrated Production of Hydrogen and C4 Chemical Products

In certain embodiments, the present invention encompasses methods for the integrated production of C4 chemicals and hydrogen.

In certain embodiments, such processes produce as final outputs, succinic anhydride (or derivatives of succinic anhydride such as succinic acid, 1,4-butanediol, THF and gamma butyrolactone) and hydrogen or products of hydrogen such as electrical energy, ammonia, or hydrogenated chemicals.

In certain embodiments, methods of the present invention comprise the steps of:

d) producing a syngas stream by steam reforming of methane or other lower aliphatic compounds;

e) feeding this syngas stream to a carbonylation reactor where the syngas stream is contacted with a substrate selected from ethylene oxide, beta propiolactone and combinations of these, in the presence of a carbonylation catalyst to deplete the syngas of at least a portion of its CO content and provide succinic anhydride as a carbonylation product; and f) recovering a hydrogen stream from the carbonylation reactor characterized in that the hydrogen stream has a higher $H_2$ to CO ratio than the syngas stream provided by step (a).

In certain embodiments, step (a) of the method above comprises steam methane reforming. In certain embodiments, such methods are characterized in that the syngas stream in step (a) has an $H_2$ to CO ratio of from about 2.8:1 to about 3.2:1. In certain embodiments, such methods are characterized in that the syngas stream in step (a) has an $H_2$ to CO ratio of about 3:1.

In certain embodiments, the method above comprises an additional step of compressing the syngas stream prior to feeding it to the carbonylation reactor. In certain embodiments, the method above comprises an additional step of removing sulfurous compounds from the syngas stream prior to feeding it to the carbonylation reactor. In certain embodiments, the method above comprises an additional step of drying the syngas stream prior to feeding it to the carbonylation reactor. In certain embodiments, the method above comprises an additional step of removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, step (b) of the method above comprises double carbonylation of ethylene oxide to produce the succinic anhydride. In certain embodiments, the double carbonylation proceeds in the presence of a single carbonylation catalyst, while in other embodiments, the double carbonylation proceeds with the aid of two or more separate catalysts.

In certain embodiments, the double carbonylation of ethylene oxide occurs in a single reactor, while in other embodiments, the two carbonylation steps occur in the two or more reactors. The utilization of two reactors is advantageous in certain embodiments, because of the kinetics of the two carbonylation steps. Without being bound by theory or thereby limiting the scope of the present invention, it is believed that carbonylation of ethylene oxide to produce beta lactones is zero order in epoxide concentration (i.e. the rate of EO conversion is independent of EO concentration. Therefore, it is believed that a continuous EO carbonylation reactor can be operated efficiently under steady state conditions and maintain a low concentration of EO in the product stream. Conversely, it is believed that the carbonylation of beta lactones is not zero order in lactone and the reaction rate is sensitive to lactone concentration. Therefore, to achieve high conversion in carbonylation of lactones it is believed this step is best performed under plug flow conditions so that a significant proportion of the lactone is consumed. Therefore, in certain embodiments of the method described above, the conversion of ethylene oxide to succinic anhydride occurs in two or more reactors. In certain embodiments, the reactors are operated under different conditions to maximize the efficiency of each of the two carbonylation steps. In certain embodiments ethylene oxide is contacted with the syngas stream in a first carbonylation reactor to provide beta propiolactone as an intermediate product which is fed to a second carbonylation reactor where it is converted to succinic anhydride. In certain embodiments of such methods, the first carbonylation reactor is a steady state reactor. In certain embodiments, the second reactor is a plug flow reactor. In certain embodiments of such methods, the first carbonylation reactor is a steady state reactor and the second reactor is a plug flow reactor. In certain embodiments, the second carbonylation reactor is fed with an upgraded syngas stream recovered from the first carbonylation reactor where the upgraded syngas stream has a higher $H_2$ to CO ratio than the syngas stream produced in step (a).

In other embodiments where the carbonylation occurs in two or more reactors, each of two carbonylation reactors is fed with the syngas stream from step (a). In certain embodiments, a hydrogen stream is obtained from each of the carbonylation reactors. In certain embodiments where multiple hydrogen streams are obtained from two or more reactors, they are combined. In other embodiments, each of the streams is used separately.

In certain embodiments, the carbonylation catalyst in step (b) of the method above comprises a metal carbonyl compound. In certain embodiments, the metal carbonyl compound is selected from any of those described in Appendix I. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described in Appendix II. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound from Appendix I and a metal complex from Appendix 11.

In certain embodiments, the method above is characterized in that the hydrogen stream recovered in step (c) has an $H_2$ to CO ratio between about 4:1 and about 1,000:1. In certain embodiments, the upgraded syngas stream recovered has an $H_2$ to CO ratio between about 5:1 and about 10:1, between about 10:1 and about 50:1, between about 50:1 and about 100:1, or between about 100:1 and about 1000:1. In certain embodiments, the hydrogen stream contains essentially no CO.

In certain embodiments, the method above is characterized in that the hydrogen stream is treated to remove one or more components prior to use. In certain embodiments, the hydrogen stream is treated to remove residual solvent prior to use. In certain embodiments, the hydrogen stream is treated to remove residual epoxide prior to use. In certain embodiments, the hydrogen stream is treated to remove carbon dioxide prior to use.

In certain embodiments, the method above is characterized in that the hydrogen stream is utilized on site for a process selected from: ammonia synthesis, powering a fuel cell, hydrogenation, and any combination of two or more of these. In certain embodiments, the hydrogen is compressed and distributed for use elsewhere.

In certain embodiments, the hydrogen stream is utilized for hydrogenation of the succinic anhydride produced in step (b). In certain embodiments, the hydrogenation of succinic anhydride from step (b) with the hydrogen stream from step (c) produces 1,4-butanediol. In certain embodiments, the hydrogenation of succinic anhydride from step (b) with the hydrogen stream from step (c) produces THF. In certain embodiments, the hydrogenation of succinic anhydride from step (b) with the hydrogen stream from step (c) produces gamma butyrolactone. Methods and catalysts for conversion of maleic and succinic anhydride or their corresponding acids to the products 1,4-BDO. THF and GBL are known in the art and can be adapted by the skilled artisan to serve in the present methods.

In certain embodiments, the method above is characterized in that the overall process has a carbon efficiency greater than 50%. That is, at least 50% of the carbon atoms fed to the steam reforming reactor are contained in products from the EO carbonylation reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

In certain embodiments, step (b) of the method above comprises two substeps. In a first substep, the syngas stream from step (a) is contacted with ethylene oxide to provide beta propiolactone along with an upgraded syngas stream having a higher $H_2$ to CO ratio than the syngas stream from step (a) and, in a second substep, the beta propiolactone is directed to a second carbonylation reactor where it is contacted with the upgraded syngas stream in the presence of a carbonylation catalyst (which may be the same as or different from the carbonylation catalyst utilized in step the method comprises an additional step of converting the beta propiolactone to succinic anhydride. In certain embodiments such methods comprise an additional step of converting the succinic anhydride to a product selected from the group consisting of: succinic acid, 1,4 butanediol, tetrahydrofuran, gamma butyrolactone, or any combination of two or more of these.

In certain embodiments where the method above comprises an additional step of converting beta propiolactone to succinic anhydride, the conversion is conducted in a second carbonylation reactor. In certain embodiments, the second carbonylation reactor is fed with the upgraded syngas stream produced in step (b) where the upgraded syngas is contacted with the beta propiolactone in the presence of a carbonylation catalyst to further deplete the upgraded syngas stream of its CO thereby providing a twice-upgraded syngas stream having a higher $H_2$ to CO ratio than the upgraded syngas stream from step (c).

VII) Integrated Production of Methanol and EO Carbonylation Products

As described above, in certain embodiments, the present invention encompasses methods for the integrated production of methanol from syngas derived from gasification.

In certain embodiments, such processes produce as final outputs, beta propiolactone or polypropiolactone (or derivatives of these such as acrylic acid, acrylate esters or superabsorbent polymers) by ethylene oxide carbonylation and methanol or methanol-derived products such dimethyl ether or olefins via a methanol-to-olefins process (MTO).

In certain embodiments, methods of the present invention comprise the steps of:
  a) Treating a carbon-based feedstock to provide a syngas stream having a $H_2$ to CO ratio less than 2:1;
  b) feeding this syngas stream to an epoxide carbonylation reactor where the syngas stream is contacted with ethylene oxide in the presence of a carbonylation catalyst to deplete the syngas of at least a portion of its CO content and provide a carbonylation product selected from the group consisting of: beta propiolactone, polypropiolactone and succinic anhydride;
  c) recovering an upgraded syngas stream from the carbonylation reactor characterized in that the upgraded stream has a higher $H_2$ to CO ratio than the syngas stream provided by step (a); and
  d) feeding the upgraded syngas stream to a methanol synthesis reactor.

In certain embodiments, step (a) of the method above comprises coal gasification. In certain embodiments, such methods are characterized in that the syngas stream in step (a) has an $H_2$ to CO ratio of from about 0.6:1 to about 0.8:1. In certain embodiments, such methods are characterized in that the syngas stream in step (a) has an $H_2$ to CO ratio of about 0.7:1.

In certain embodiments, step (a) of the method above comprises biomass gasification. In certain embodiments, the biomass is selected from the group consisting of: corn stover, sugar cane bagasse, switch grass, municipal solid waste, and wood waste. In certain embodiments, such methods are characterized in that the syngas stream in step (a) has an $H_2$ to CO ratio of from about 0.4:1 to about 0.8:1. In certain embodiments, such methods are characterized in that the syngas stream in step (a) has an $H_2$ to CO ratio of about 0.6:1. In certain embodiments, such methods are characterized in that the syngas stream in step (a) has an $H_2$ to CO ratio of about 0.5:1.

In certain embodiments, the method above comprises an additional step of compressing the syngas stream prior to feeding it to the carbonylation reactor. In certain embodiments, the method above comprises an additional step of removing sulfurous compounds from the syngas stream prior to feeding it to the carbonylation reactor. In certain embodiments, the method above comprises an additional step of drying the syngas stream prior to feeding it to the carbonylation reactor. In certain embodiments, the method above comprises an additional step of removing $CO_2$ from the syngas stream prior to feeding it to the carbonylation reactor. In certain embodiments, the method above is characterized in that $CO_2$ is not removed from the syngas stream prior to feeding it to the carbonylation reactor.

In certain embodiments, the product of step (b) of the method above comprises beta propiolactone and the method comprises an additional step of converting the beta propiolactone to acrylic acid, or acrylate esters.

In certain embodiments, the product of step (b) of the method above comprises beta propiolactone and the method comprises an additional step of converting the beta propiolactone to succinic anhydride. In certain embodiments such methods comprise an additional step of converting the succinic anhydride to a product selected from the group consisting of: succinic acid, 1,4 butanediol, tetrahydrofuran, gamma butyrolactone, or any combination of two or more of these.

In certain embodiments where the method above comprises an additional step of converting beta propiolactone to succinic anhydride, the conversion is conducted in a second carbonylation reactor. In certain embodiments, the second carbonylation reactor is also fed with the syngas stream produced in step (a) where it is contacted with the beta propiolactone in the presence of a carbonylation catalyst to deplete the syngas of at least a portion of its CO content and provide succinic anhydride as a second carbonylation product. In certain embodiments, a second upgraded syngas stream, characterized in that it has a higher $H_2$ to CO ratio that the syngas stream produced in step (a) is recovered from the second carbonylation reactor. In certain embodiments, the first and second upgraded syngas streams are combined and utilized in step (d).

In certain embodiments where the method above comprises an additional step of converting beta propiolactone to succinic anhydride, the conversion is conducted in a second carbonylation reactor which is fed with the upgraded syngas stream produced in step (b) where it is contacted with the beta propiolactone in the presence of a carbonylation catalyst to further deplete the upgraded syngas stream of its CO thereby providing a twice-upgraded syngas stream having a higher $H_2$ to CO ratio than the upgraded syngas stream from step (c). In certain embodiments, the method comprises an additional step of recovering the twice upgraded syngas stream from the second carbonylation reactor and feeding it to the methanol reactor in step (d).

In certain embodiments, the product of step (b) of the method above is polypropiolactone and the method comprises an additional step of pyrolyzing the polypropiolactone to produce acrylic acid.

In certain embodiments, the carbonylation catalyst in step (b) of the method above comprises a metal carbonyl compound. In certain embodiments, the metal carbonyl compound is selected from any of those described in Appendix I. In certain embodiments, the metal carbonyl compound comprises a cobalt carbonyl compound. In certain embodiments, metal carbonyl compound comprises a rhodium carbonyl compound. In certain embodiments, the carbonylation catalyst in step (b) of the method above comprises a metal carbonyl compound in combination with another component selected from the group consisting of: organic bases, neutral Lewis acids, and cationic Lewis acids. In certain embodiments, the carbonylation catalyst in step (b) of the method above comprises an anionic cobalt carbonyl compound in combination with a cationic Lewis acid. In certain embodiments, such cationic Lewis acids comprise metal ligand complexes. In certain embodiments, the metal ligand complexes comprise any complex described in Appendix II. In certain embodiments, such metal ligand complexes comprise a metal atom coordinated to a multidentate ligand. In certain embodiments, such metal ligand complexes comprise an aluminum or chromium atom. In certain embodiments, such metal ligand complexes comprise a porphyrin or salen ligand. In certain embodiments, the carbonylation catalyst in step (b) of the method above comprises any combination of a metal carbonyl compound from Appendix I and a metal complex from Appendix II.

In certain embodiments, step (c) in the method above is characterized in that the upgraded syngas stream recovered has an $H_2$ to CO ratio between about 1.2:1 and about 3:1. In certain embodiments, the upgraded syngas stream recovered has an $H_2$ to CO ratio between about 1.6:1 and about 2.8:1, between about 1.8:1 and about 2.6:1, between about 1.8:1 and about 2.2:1, or between about 1.9:1 and about 2.1:1. In certain embodiments, the upgraded syngas stream recovered has an $H_2$ to CO ratio of about 2:1.

In certain embodiments, the method above is characterized in that the reaction pressure in the carbonylation reactor is higher than the reaction pressure in the methanol synthesis reactor. In certain embodiments, the upgraded syngas stream is fed to the methanol synthesis reactor without an intermediate compression step. In certain embodiments, the upgraded syngas stream exits the carbonylation reactor via a backpressure regulator and is fed directly to the methanol synthesis reactor.

In certain embodiments, the method above is characterized in that the upgraded syngas stream is treated to remove one or more components prior to use in the methanol synthesis step. In certain embodiments, the upgraded syngas stream is treated to remove residual solvent prior to feeding the stream to the methanol synthesis reactor. In certain embodiments, the upgraded syngas stream is treated to remove residual epoxide prior to feeding the stream to the methanol synthesis reactor. In certain embodiments, the upgraded syngas stream is treated to remove carbon dioxide prior to feeding the stream to the methanol synthesis reactor.

In certain embodiments, the method above is characterized in that the methanol synthesis reactor in step (d) utilizes a catalyst comprising one or more of, copper, alumina and zinc oxide.

In certain embodiments, the method above comprises an additional step of feeding methanol produced in the methanol reactor to an MTO reactor where it is converted to olefins. In certain embodiments, the MTO reactor converts the methanol to ethylene, propylene or a mixture of ethylene and propylene.

In embodiments where the process is integrated to an MTO reactor, the possibility exists for a process that produces carbonylation products derived entirely from the carbon source fed to the syngas production step. This is achieved by utilizing ethylene or propylene from the MTO stage to produce ethylene oxide or propylene oxide which is then utilized as the feedstock for the carbonylation reactor.

Figure 5:
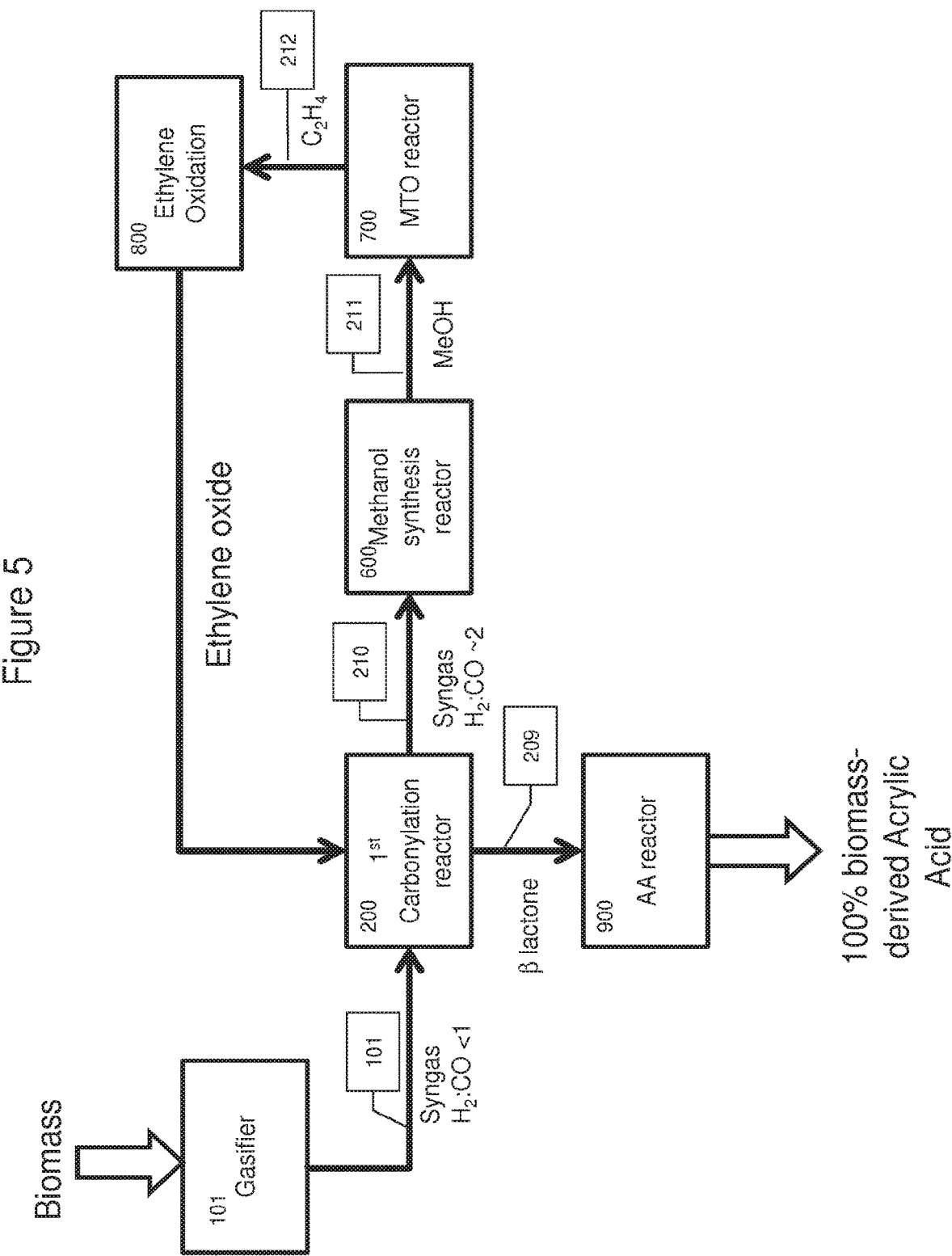
FIG. 5 shows a schematic of a process according to the present invention for the production of acrylic acid from biomass

Therefore, in certain embodiments, the present invention encompasses methods for the production of 100% biomass-derived chemicals. In certain embodiments such chemicals are the result of the process depicted in FIG. 5. FIG. 5 shows an integrated process for production of acrylic acid from biomass. As shown, biomass is gasified in Gasifier 101 to produce a syngas stream 101 having an $H_2$:CO ratio less than 1 (typically 0.5-0.7:1). This is fed to Carbonylation Reactor 200 where it is contacted with ethylene oxide in the presence of carbonylation catalyst. Carbonylation reactor produces beta propiolactone stream 209 along with upgraded syngas stream 210. Upgraded syngas stream 210 has an H2 to CO ratio around 2:1 and is therefore suitable for use in methanol synthesis reactor 600. The methanol from reactor 600 is fed to MTO reactor 700 where it is converted to ethylene stream 212 (and optionally additional streams such as propylene and higher olefins, not shown). Ethylene stream 212 is directed to an oxidation reactor 800 where it is converted to ethylene oxide. The resulting ethylene oxide is fed to carbonylation reactor 200 to react with syngas stream 101. To complete the acrylic acid synthesis the beta lactone stream 209 from the carbonylation reactor is fed to AA reactor 900 where it is converted to acrylic acid. The three carbon atoms in the resulting AA are all derived from the biomass fed to reactor 101:

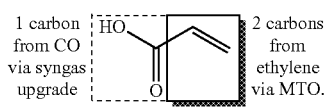

In one aspect, the present invention encompasses acrylic acid wherein all three carbon atoms are derived from biomass in an integrated gasification process characterized in that the carboxylic carbon atom is derived from CO in the syngas, and the two ethylene carbon atoms are derived from ethylene produced by MTO utilizing methanol formed from a syngas stream upgraded to increase its H2 content by carbonylation of the epoxide.

A closely related process provides biomass derived polymers such as polypropiolactone (PPL) or poly(3-hydroxybutyrolactone) (PHB). Such processes either add a beta lactone polymerization reactor fed by the beta lactone stream, or utilize conditions in the carbonylation reactor to produce polyester as the primary product. For the PHB process, the MTO reactor would be operated to provide a propylene stream which is then oxidized to propylene oxide which is fed to the carbonylation reactor.

Figure 6:
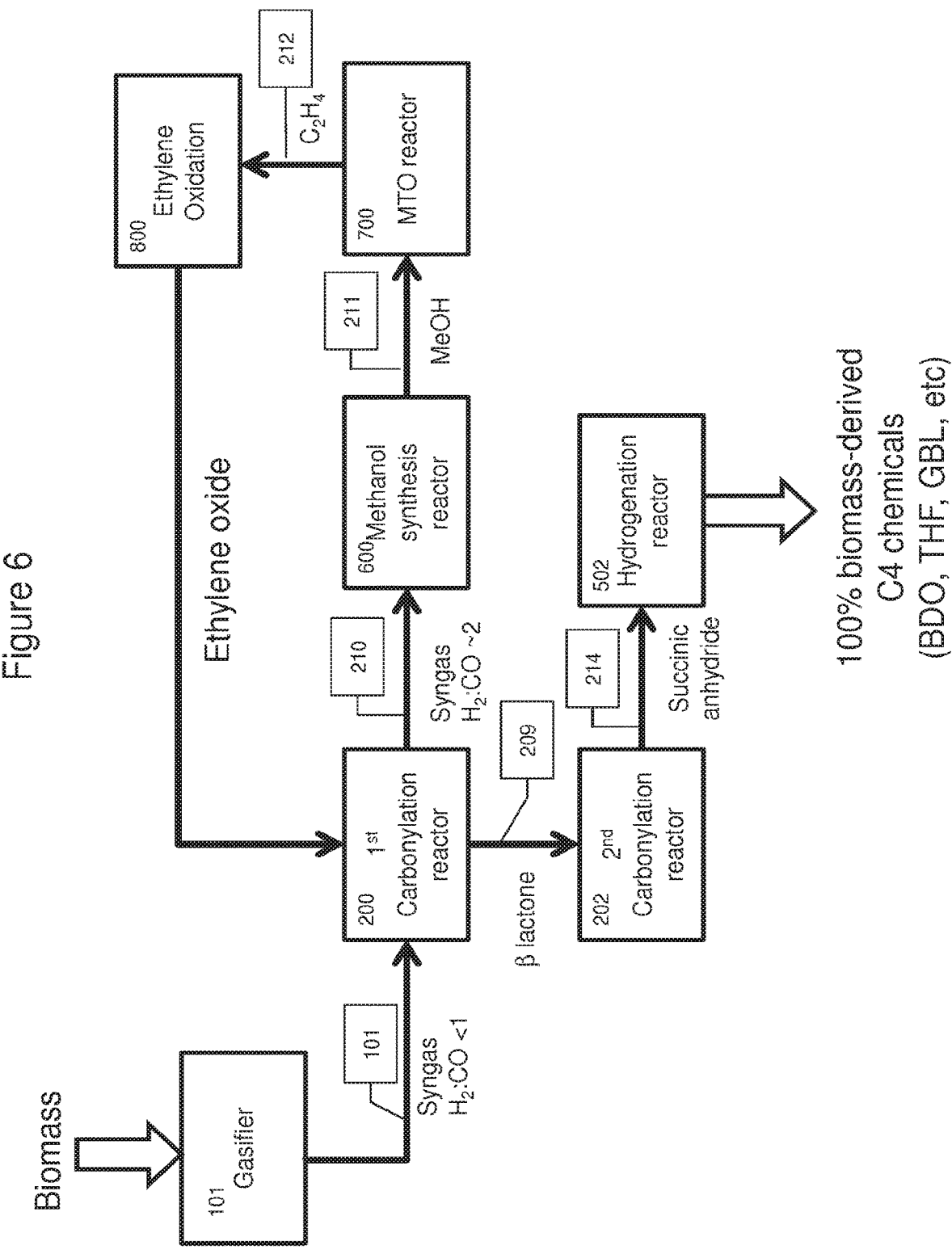
FIG. 6 shows a schematic of a process according to the present invention for the production of C4 chemicals from biomass

In certain other embodiments, the present invention encompasses methods for the production of 100% biomass-derived C4 chemicals. In certain embodiments such chemicals are the result of the process depicted in FIG. 6. FIG. 6 shows an integrated process for production of acrylic acid from biomass. As shown, biomass is gasified in Gasifier 101 to produce a syngas stream 101 having an $H_2$:CO ratio less than 1 (typically 0.5-0.7:1). This is fed to Carbonylation Reactor 200 where it is contacted with ethylene oxide in the presence of carbonylation catalyst. Carbonylation reactor produces beta propiolactone stream 209 along with upgraded syngas stream 210. Upgraded syngas stream 210 has an H2 to CO ratio around 2:1 and is therefore suitable for use in methanol synthesis reactor 600. The methanol from reactor 600 is fed to MTO reactor 700 where it is converted to ethylene stream 212 (and optionally additional streams such as propylene and higher olefins, not shown). Ethylene stream 212 is directed to an oxidation reactor 800 where it is converted to ethylene oxide. The resulting ethylene oxide is fed to carbonylation reactor 200 to react with syngas stream 101. To complete the C4 chemicals synthesis, the beta lactone stream 209 from the carbonylation reactor is fed to $2^{nd}$ carbonylation reactor 202 where it is converted to succinic anhydride. Succinic anhydride stream 214 is fed to hydrogenation reactor where it is converted to C4 commodity chemicals such as 1,4 butanediol, tetrahydrofuran. GBL, or combinations of two or more of these. The three carbon atoms in the resulting chemicals are all derived from the biomass fed to reactor 101:

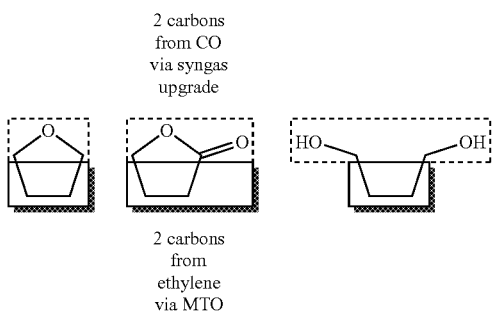

In one aspect, the present invention encompasses C4 chemicals (THF, BDO and/or GBL) wherein all four carbon atoms are derived from biomass in an integrated gasification process characterized in that the carbon atoms boned to oxygen atoms are derived from CO in syngas, and the two other carbon atoms are derived from ethylene produced by MTO utilizing methanol formed from a syngas stream upgraded to increase its $H_2$ content by carbonylation of the epoxide.

In certain embodiments, the method above is characterized in that the overall process has a carbon efficiency greater than 50%. That is, at least 50% of the carbon atoms fed to the syngas production step are contained in the combined products from the EO carbonylation reactor and the methanol synthesis reactor. In certain embodiments, the method is characterized in that the overall process has a carbon efficiency greater than 55%, greater than 60%, greater than 62%, greater than 63%, greater than 64%, or greater than 65%. In certain embodiments, the method is characterized in that the overall process has a carbon efficiency greater than 66%, greater than 67%, greater than 68%, greater than 69%, or greater than 70%. In certain embodiments, the method is characterized in that the overall process has a carbon efficiency between about 50% and about 60%. In certain embodiments, the method is characterized in that the overall process has a carbon efficiency between about 55% and about 60%. In certain embodiments, the method is characterized in that the overall process has a carbon efficiency between about 60% and about 64%. In certain embodiments, the method is characterized in that the overall process has a carbon efficiency between about 64% and about 67%. In certain embodiments, the method is characterized in that the overall process has a carbon efficiency between about 67% and about 70%.

In certain embodiments, the method above is characterized in that the methanol synthesis process in step (d) is fed with syngas from the gasification process in step (a) without utilizing the water gas shift reaction to increase its $H_2$ to CO ratio.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

APPENDIX I

Metal Carbonyl Compounds Suitable for Certain Methods of the Invention

In certain embodiments, a provided metal carbonyl compound comprises an anionic metal carbonyl moiety. In other embodiments, a provided metal carbonyl compound comprises a neutral metal carbonyl compound. In certain embodiments, a provided metal carbonyl compound comprises a metal carbonyl hydride or a hydrido metal carbonyl compound. In some embodiments, a provided metal carbonyl compound acts as a pre-catalyst which reacts in situ with one or more reaction components to provide an active species different from the compound initially provided. Such pre-catalysts are specifically encompassed by the present invention as it is recognized that the active species in a given reaction may not be known with certainty.

In certain embodiments, the metal carbonyl compound comprises an anionic metal carbonyl species. In certain embodiments, such anionic metal carbonyl species have the general formula $[Q_dM'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In certain embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In certain embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$ $[V(CO)_6]^-$ $[Rh(CO)_4]^-$, $[Fe(CO)_4]^{2-}$ $[Ru(CO)_4]^{2-}$, $[Os(CO)_4]^{2-}$ $[Cr_2(CO)_{10}]^{2-}$ $[Fe_2(CO)_8]^{2-}$ $[Tc(CO)_5]^-$ $[Re(CO)_5]^-$ and $[Mn(CO)_5]^-$. In certain embodiments, the anionic metal carbonyl comprises $[Co(CO)_4]^-$. In some embodiments, a mixture of two or more anionic metal carbonyl complexes may be present in the polymerization system.

The term "such as to provide a stable anionic metal carbonyl" for $[Q_dM'_e(CO)_w]^{y-}$ is used herein to mean that $[Q_dM'_e(CO)_w]^{y-}$ is a species characterizable by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for CO to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments where the provided metal carbonyl compound is an anionic species, one or more cations must also necessarily be present. The present invention places no particular constraints on the identity of such cations. For example, in certain embodiments, the metal carbonyl anion is associated with a cationic Lewis acid. In other embodiments, a cation associated with a provided anionic metal carbonyl compound is a simple metal cation such as those from Groups 1 or 2 of the periodic table (e.g. $Na^+$, $Li^+$, $K^+$, $Mg^{2+}$ and the like). In other embodiments a cation associated with a provided anionic metal carbonyl compound is a bulky non electrophilic cation such as an 'onium salt' (e.g. $Bu_4N^+$, $PPN^+$, $Ph_4P^+$ $Ph_4As^+$, and the like.

In certain embodiments, a provided metal carbonyl compound comprises a neutral metal carbonyl. In certain embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In certain embodiments, the neutral metal carbonyl has the general formula $QM'(CO)_{w'}$. In certain embodiments, the neutral metal carbonyl has the general formula $M'(CO)_{w'}$. In certain embodiments, the neutral metal carbonyl has the general formula $QM'_2(CO)_{w'}$. In certain embodiments, the neutral metal carbonyl has the general formula $M'_2(CO)_{w'}$. Suitable neutral metal carbonyl compounds include, but are not limited to: $Ti(CO)_7$; $V_2(CO)_{12}$; $Cr(CO)_6$; $Mo(CO)_6$; $W(CO)_6Mn_2(CO)_{10}$, $Te_2(CO)_{10}$, and $Re_2(CO)_{10}$ $Fe(CO)_5$, $Ru(CO)_5$ and $Os(CO)_5$ $Ru_3(CO)_{12}$, and $Os_3(CO)_{12}$ $Fe_3(CO)_{12}$ and $Fe_2(CO)_9$ $Co_4(CO)_{12}$, $Rh_4(CO)_{12}$, $Rh_6(CO)_{16}$, and $Ir_4(CO)_{12}$, $Co_2(CO)_8$ $Ni(CO)_4$.

The term "such as to provide a stable neutral metal carbonyl for $Q_dM'_e(CO)_{w'}$ is used herein to mean that $Q_dM'_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for CO to coordinate and therefore the value of w'. Typically, such compounds conform to stoichiometries conforming to the "18-electron rule". Such knowledge is within the grasp of one having ordinary skill in the arts pertaining to the synthesis and characterization of metal carbonyl compounds.

In certain embodiments, one or more of the CO ligands of any of the metal carbonyl compounds described above is replaced with a ligand Q. In certain embodiments, Q is a phosphine ligand. In certain embodiments, Q is a triaryl phosphine. In certain embodiments, Q is trialkyl phosphine. In certain embodiments, Q is a phosphite ligand. In certain embodiments, Q is an optionally substituted cyclopentadienyl ligand. In certain embodiments, Q is cp. In certain embodiments, Q is cp*.

In certain embodiments, polymerization systems of the present invention comprise hydrido metal carbonyl compounds. In certain embodiments, such compounds are provided as the hydrido metal carbonyl compound, while in other embodiments, the hydrido metal carbonyl is generated in situ by reaction with hydrogen gas, or with a protic acid using methods known in the art (see for example *Chem. Rev.,* 1972, 72 (3), pp 231-281 DOI: 10.1021/cr60277a003, the entirety of which is incorporated herein by reference).

In certain embodiments, the hydrido metal carbonyl (either as provided or generated in situ) comprises one or more of $HCo(CO)_4$, $HCoQ(CO)_3$, $HMn(CO)_5$, $HMn(CO)_4Q$, $HW(CO)_3Q$, $HRe(CO)_5$, $HMo(CO)_3Q$, $HOs(CO)_2Q$, $HMo(CO)_2Q_2$, $HFe(CO_2)Q$, $HW(CO)_2Q_2$, $HRuCOQ_2$, $H_2Fe(CO)_4$ or $H_2Ru(CO)_4$, where each Q is independently as defined above and in the classes and subclasses herein. In certain embodiments, the metal carbonyl hydride (either as provided or generated in situ) comprises $HCo(CO)_4$. In certain embodiments, the metal carbonyl hydride (either as provided or generated in situ) comprises $HCo(CO)_3PR_3$, where each R is independently an optionally substituted aryl group, an optionally substituted $C_{1-20}$ aliphatic group, an optionally substituted $C_{1-10}$ alkoxy group, or an optionally substituted phenoxy group. In certain embodiments, the metal carbonyl hydride (either as provided or generated in situ) comprises $HCo(CO)_3cp$, where cp represents an optionally substituted pentadienyl ligand. In certain embodiments, the metal carbonyl hydride (either as provided or generated in situ) comprises $HMn(CO)_5$. In certain embodiments, the metal carbonyl hydride (either as provided or generated in situ) comprises $H_2Fe(CO)_4$.

In certain embodiments, for any of the metal carbonyl compounds described above, M' comprises a transition metal. In certain embodiments, for any of the metal carbonyl compounds described above, M' is selected from Groups 5 (Ti) to 10 (Ni) of the periodic table. In certain embodiments, M' is a Group 9 metal. In certain embodiments, M' is Co. In certain embodiments. M' is Rh. In certain embodiments, M' is Ir. In certain embodiments, M' is Fe. In certain embodiments, M' is Mn.

APPENDIX II

Lewis Acidic Metal Complexes Suitable for Certain Methods of the Invention

In certain embodiments where a carbonylation catalyst utilized in any of the methods above comprises a metal carbonyl compound in combination with a cationic Lewis acid, the Lewis acid has a formula $[(L^e)_vM_b]^{z+}$, where:

$L^e$ is a ligand where, when two or more $L^e$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In certain embodiments, provided Lewis acids conform to structure I:

I wherein:

is a multidentate ligand;

M is a metal atom coordinated to the multidentate ligand;

a is the charge of the metal atom and ranges from 0 to 2; and

In certain embodiments, provided metal complexes conform to structure II:

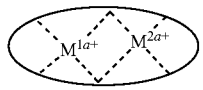
II

Where a is as defined above (each a may be the same or different), and $M^1$ is a first metal atom;

$M^2$ is a second metal atom;

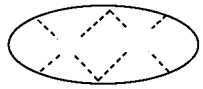

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In certain embodiments, the multidentate ligand is a salen derivative. In other embodiments, the multidentate ligand is a porphyrin derivative. In other embodiments, the multidentate ligand is a tetraphenylporphyrin derivative. In other embodiments, the multidentate ligand is a corrole derivative.

1

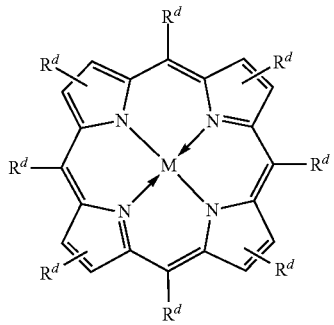

2

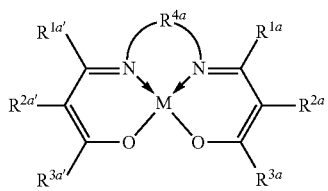

-continued

3

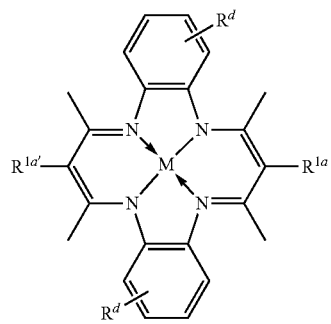

4

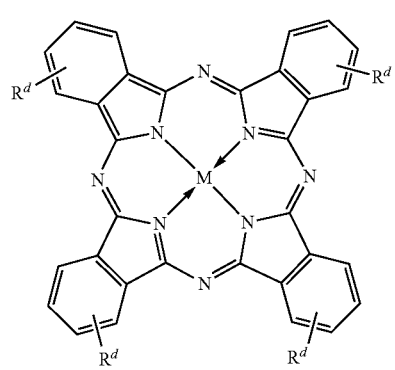

5

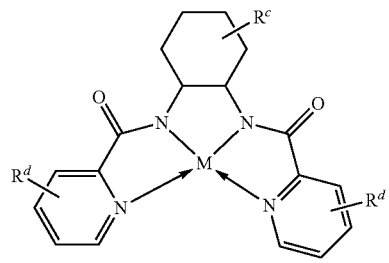

6

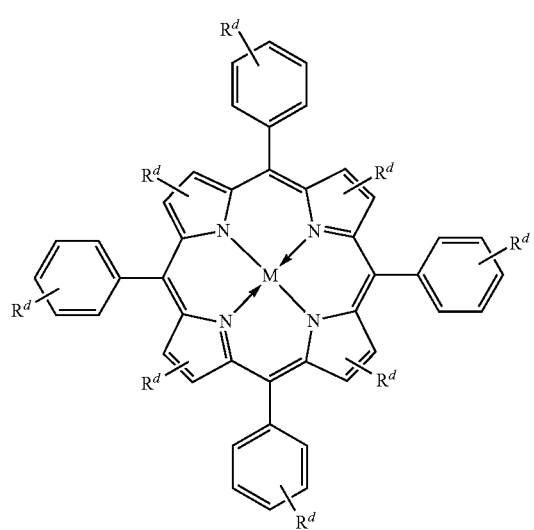

-continued

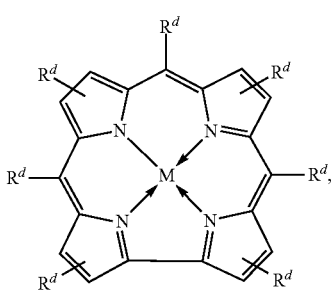

7 where each of $R^c$, $R^d$, $R^a$, $R^{1a}$, $R^{2a}$, $R^{3a}$, $R^{1a'}$, $R^{2a'}$, $R^{3a'}$, and M, is as defined and described in the classes and subclasses herein.

In certain embodiments, Lewis acids provided in polymerization systems of the present invention comprise metalporphinato complexes. In certain embodiments, the moiety

has the structure:

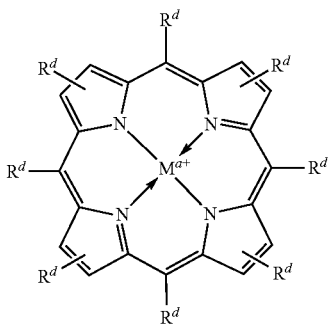

where each of M and a is as defined above and described in the classes and subclasses herein, and $R^d$ at each occurrence is independently hydrogen, halogen, —$OR^4$, —$NR^y{}_2$, —SR, —CN, —$NO_2$, —$SO_2R^y$, —$SOR^y$, —$SO_2NR^y{}_2$: —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, where each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ independently is a hydroxyl protecting group or $R^y$.

In certain embodiments, the moiety

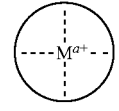

has the structure:

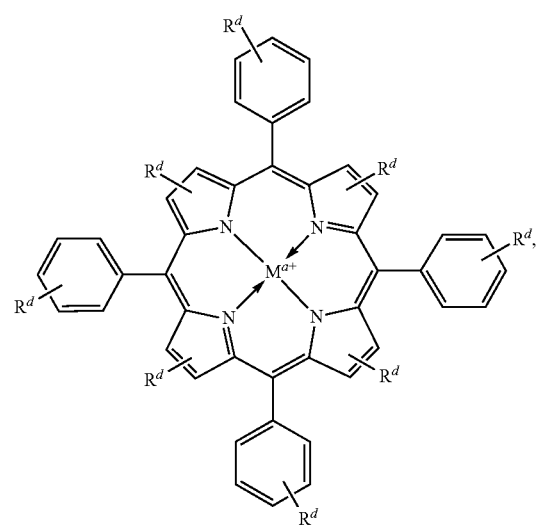

where M, a and $R^d$ are as defined above and in the classes and subclasses herein.

In certain embodiments, the moiety as the structure:

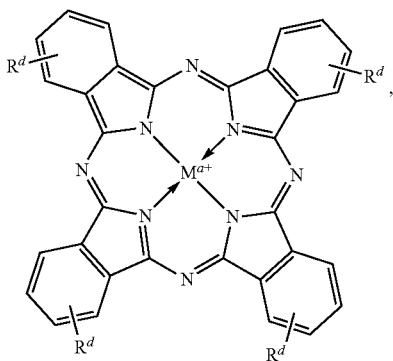

where M, a and $R^d$ are as defined above and in the classes and subclasses herein.

In certain embodiments, Lewis acids included in polymerization systems of the present invention comprise metallo salenate complexes. In certain embodiments, the moiety

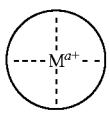

has the structure:

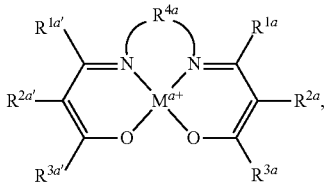

wherein:
M, and a are as defined above and in the classes and subclasses herein.

$R^{1a}$, $R^{1a'}$, $R^{2a}$, $R^{2a'}$, $R^{3a}$, and $R^{3a'}$ are independently hydrogen, halogen, —$OR^4$, —$NR^y_2$, —SR, —CN, —$NO_2$, —$SO_2R^y$, —SOR, —$SO_2NR^y_2$; —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each R, $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more R groups; and $R^{4a}$ is selected from the group consisting of:

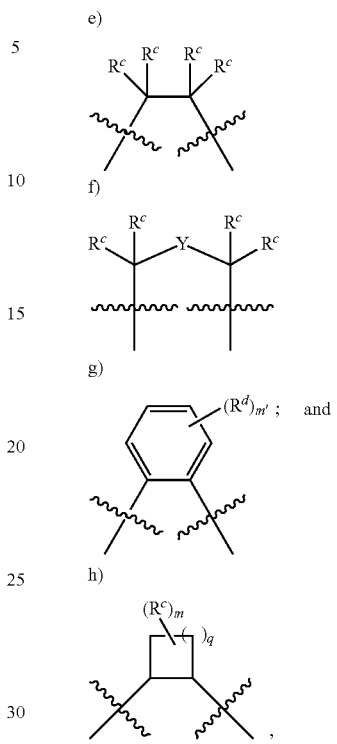

where
$R^c$ at each occurrence is independently hydrogen, halogen, —OR, —$NR^y_2$, —$SR^y$, —CN, —$NO_2$, —$SO_2R^y$, —$SOR^y$, —$SO_2NR^y_2$; —CNO, —$NRSO_2R^y$, —NCO, —$N_3$, —$SiR_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur, and 4- to 7-membered heterocyclic having 1-2 heteroatoms independently selected from the group consisting of nitrogen, oxygen, and sulfur;
where:
two or more $R^c$ groups may be taken together with the carbon atoms to which they are attached and any intervening atoms to form one or more rings;
when two $R^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;
Y is a divalent linker selected from the group consisting of: —$NR^y$—, —N(R)C(O)—, —C(O)$NR^y$—, —O—, —C(O)—, —OC(O)—, —C(O)O—, —S—, —SO—, —$SO_2$—, —C(=S)—, —C(=$NR^y$)—, —N=N—; a polyether; a $C_3$ to $C_8$ substituted or unsubstituted carbocycle; and a $C_1$ to $C_8$ substituted or unsubstituted heterocycle;
m' is 0 or an integer from 1 to 4, inclusive;
q is 0 or an integer from 1 to 4, inclusive; and
x is 0, 1, or 2.

In certain embodiments, a provided Lewis acid comprises a metallo salen compound, as shown in formula Ia:

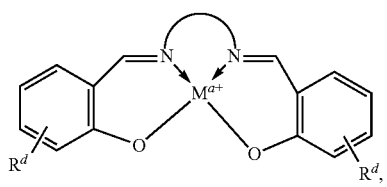

Ia wherein each of M, $R^d$, and a, is as defined above and in the classes and subclasses herein,

represents is an optionally substituted moiety linking the two nitrogen atoms of the diamine portion of the salen ligand, where

is selected from the group consisting of a $C_3$-$C_{14}$ carbocycle, a $C_6$-$C_{10}$ aryl group, a $C_3$-$C_{14}$ heterocycle, and a $C_5$-$C_{10}$ heteroaryl group; or an optionally substituted $C_{2-20}$ aliphatic group, wherein one or more methylene units are optionally and independently replaced by —$NR^y$—, —$N(R^y)C(O)$—, —$C(O)N(R^y)$—, —$OC(O)N(R^y)$—, —$N(R^y)C(O)O$—, —$OC(O)O$—, —O—, —$C(O)$—, —$OC(O)$—, —$C(O)O$—, —S—, —SO—, —$SO_2$—, —$C(=S)$—, —$C(=NR^y)$—, —$C(=NOR^y)$— or —N=N—.

In certain embodiments metal complexes having formula Ia above, at least one of the phenyl rings comprising the salicylaldehyde-derived portion of the metal complex is independently selected from the group consisting of:

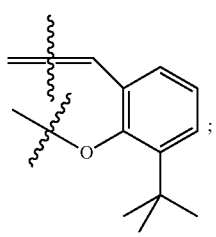;
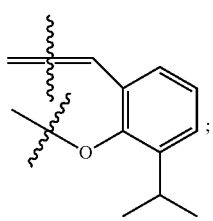;
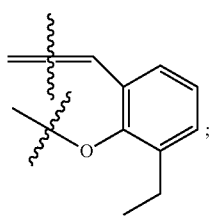;
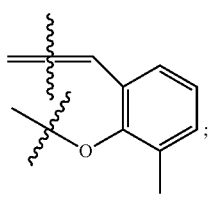;

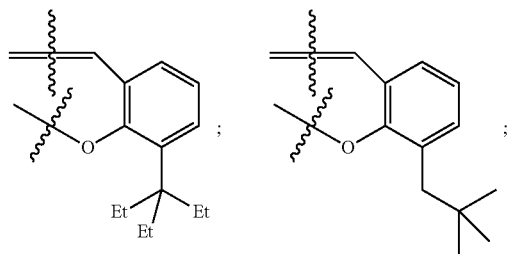
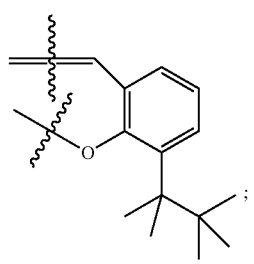;
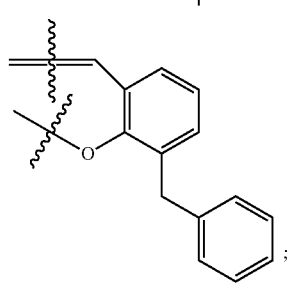;
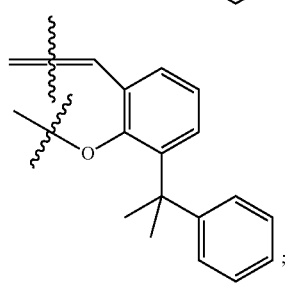;
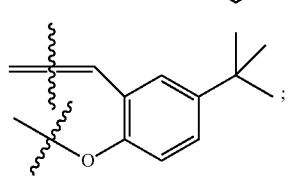;
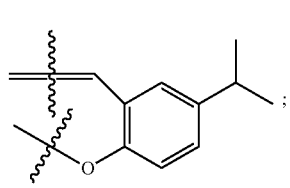;
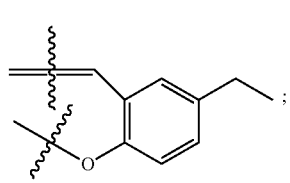;

-continued
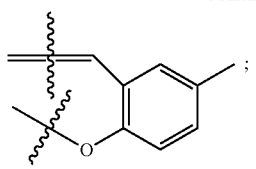
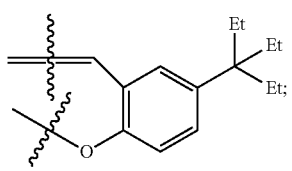
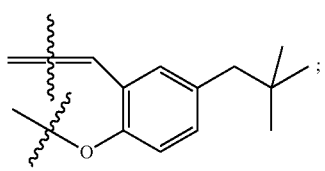
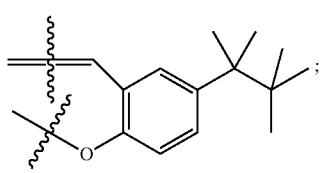
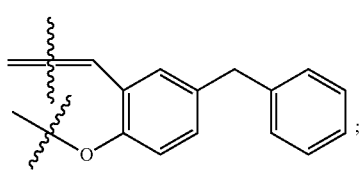
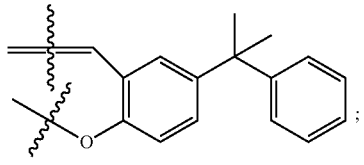
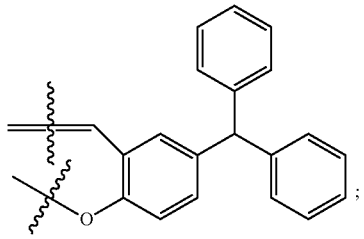
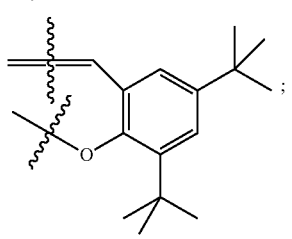
-continued
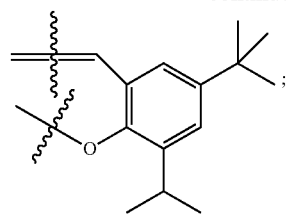
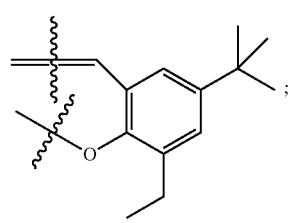
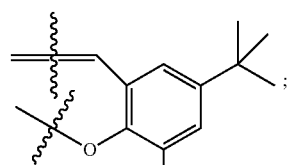
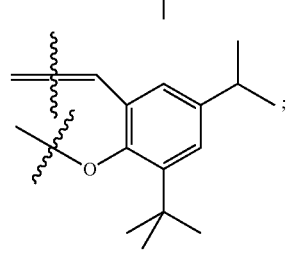
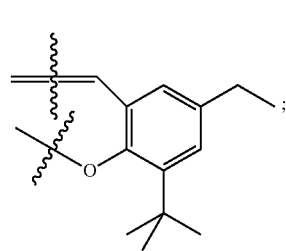
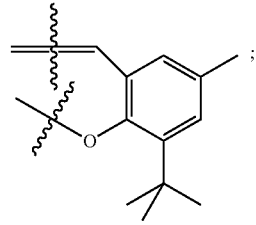
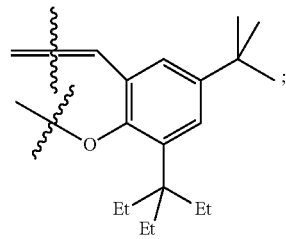

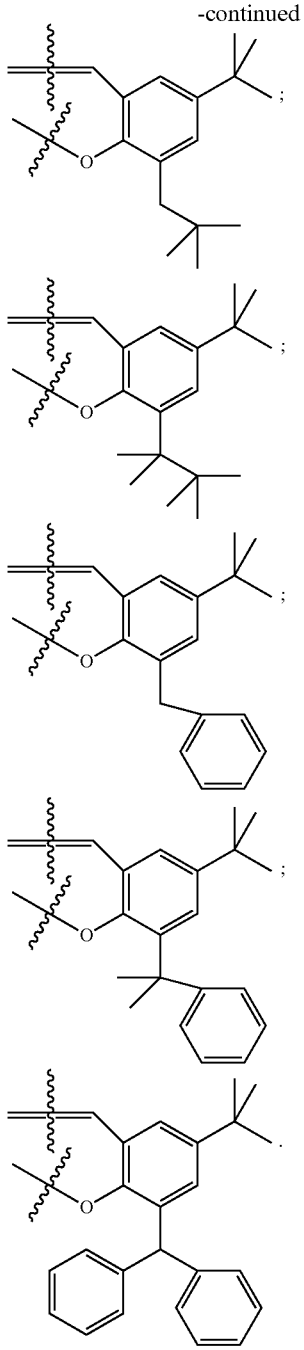

In certain embodiments, a provided Lewis acid comprises a metallo salen compound, conforming to one of formulae Va or Vb:

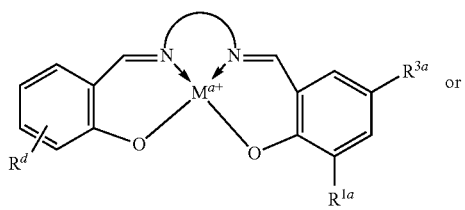

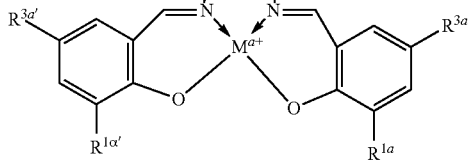

where M, a, $R^d$, $R^{1a}$, $R^{3a}$, $R^{1a'}$, $R^{3a'}$, and

are as defined above and in the classes and subclasses herein.

In certain embodiments of metal complexes having formulae Va or Vb, each $R^{1'}$ and $R^{3'}$ is, independently, optionally substituted $C_1$-$C_{20}$ aliphatic.

In certain embodiments, the moiety

comprises an optionally substituted 1,2-phenyl moiety.

In certain embodiments, Lewis acids included in polymerization systems of the present invention comprise metal-tmtaa complexes. In certain embodiments, the moiety

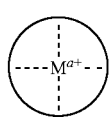

has the structure:

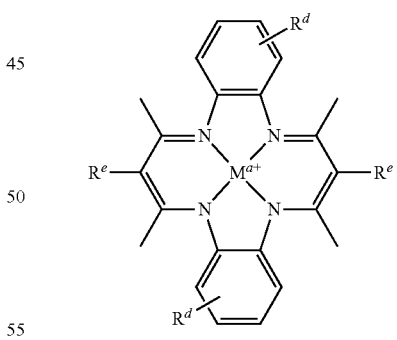

where M, a and $R^d$ are as defined above and in the classes and subclasses herein, and $R^e$ at each occurrence is independently hydrogen, halogen, —OR, —NR$_2$, —SR, —CN, —NO$_2$, —SO$_2$R, —SOR, —SO$_2$NR$_2$; —CNO, —NRSO$_2$R, —NCO, —N$_3$, —SiR$_3$; or al optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In certain embodiments, the moiety

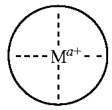

has the structure:

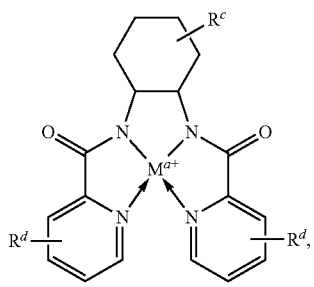

where each of M, a, $R^c$ and $R^d$ is as defined above and in the classes and subclasses herein.

In certain embodiments, where polymerization systems of the present invention include a Lewis acidic metal complex, the metal atom is selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium.

In certain embodiments. M has an oxidation state of +2. In certain embodiments, M is Zn(II), Cu(II), Mn(II), Co(II), Ru(II), Fe(II), Co(II), Rh(II), Ni(II), Pd(II) or Mg(II). In certain embodiments M is Zn(II). In certain embodiments M is Cu(II).

In certain embodiments. M has an oxidation state of +3. In certain embodiments, M is Al(III), Cr(III), Fe(III), Co(III), Ti(III) In(III), Ga(III) or Mn(III). In certain embodiments M is Al(III). In certain embodiments M is Cr(III).

In certain embodiments, M has an oxidation state of +4. In certain embodiments, M is Ti(IV) or Cr(IV).

In certain embodiments, $M^1$ and $M^2$ are each independently a metal atom selected from the periodic table groups 2-13, inclusive. In certain embodiments, M is a transition metal selected from the periodic table groups 4, 6, 11, 12 and 13. In certain embodiments, M is aluminum, chromium, titanium, indium, gallium, zinc cobalt, or copper. In certain embodiments, M is aluminum. In other embodiments, M is chromium. In certain embodiments, $M^1$ and $M^2$ are the same. In certain embodiments, $M^1$ and $M^2$ are the same metal, but have different oxidation states. In certain embodiments, $M^1$ and $M^2$ are different metals.

In certain embodiments, one or more of $M^1$ and $M^2$ has an oxidation state of +2. In certain embodiments, $M^1$ is Zn(II), Cu(II), Mn(II), Co(II), Ru(II), Fe(II), Co(II), Rh(II), Ni(II), Pd(II) or Mg(II). In certain embodiments $M^1$ is Zn(II). In certain embodiments $M^1$ is Cu(II). In certain embodiments, $M^2$ is Zn(II), Cu(II), Mn(II), Co(II), Ru(II), Fe(II), Co(II), Rh(II), Ni(II), Pd(II) or Mg(II). In certain embodiments $M^2$ is Zn(II). In certain embodiments $M^2$ is Cu(II).

In certain embodiments, one or more of $M^1$ and $M^2$ has an oxidation state of +3. In certain embodiments, $M^1$ is Al(III), Cr(III), Fe(III), Co(III), Ti(III) In(III), Ga(III) or Mn(III). In certain embodiments $M^1$ is Al(III). In certain embodiments $M^1$ is Cr(III). In certain embodiments, $M^2$ is Al(III), Cr(III), Fe(III), Co(III), Ti(III) In(III), Ga(III) or Mn(III). In certain embodiments $M^2$ is Al(III). In certain embodiments $M^2$ is Cr(III).

In certain embodiments, one or more of $M^1$ and $M^2$ has an oxidation state of +4. In certain embodiments, $M^1$ is Ti(IV) or Cr(IV). In certain embodiments, $M^2$ is Ti(IV) or Cr(IV).

In certain embodiments, one or more neutral two electron donors coordinate to M $M^1$ or $M^2$ and fill the coordination valence of the metal atom. In certain embodiments, the neutral two electron donor is a solvent molecule. In certain embodiments, the neutral two electron donor is an ether. In certain embodiments, the neutral two electron donor is tetrahydrofuran, diethyl ether, acetonitrile, carbon disulfide, or pyridine. In certain embodiments, the neutral two electron donor is tetrahydrofuran. In certain embodiments, the neutral two electron donor is an epoxide. In certain embodiments, the neutral two electron donor is an ester or a lactone.

What is claimed is:

1. A method for the integrated production of chemicals comprising the steps of:
   a) in a first reaction zone, contacting an epoxide in the presence of a carbonylation catalyst with a syngas stream containing hydrogen and carbon monoxide thereby causing carbon monoxide in the industrial gas stream to react with the epoxide to provide an epoxide carbonylation product,
   b) removing an upgraded gas stream from the first reaction zone wherein the upgraded gas stream has a higher hydrogen to carbon monoxide than the starting syngas stream, and
   c) in a second reaction zone, utilizing the upgraded gas stream to conduct a second chemical process requiring a hydrogen to CO ratio higher than the ratio in the industrial gas stream utilized in step (a).

2. The method of claim 1, wherein the syngas stream has a molar hydrogen to CO ratio between 0.5:1 and 1.2:1, and the upgraded gas stream has a hydrogen to CO ratio of at least 1.9:1.

3. The method of claim 1, wherein the second chemical process comprises Fischer Tropsch synthesis.

4. The method of claim 1, wherein the second chemical process comprises reaction on a fuel cell.

5. The method of claim 1, wherein the second chemical process comprises hydrogenation.

6. The method of claim 1, wherein the epoxide carbonylation product is selected from the group consisting of: optionally substituted beta lactone, optionally substituted succinic anhydride, and a polyester resulting from alternating polymerization of CO and the epoxide.

7. The method of claim 1, wherein the epoxide is ethylene oxide.

8. The method of claim 7, wherein the carbonylation product is beta propiolactone.

9. The method of claim 7, wherein the epoxide carbonylation product is succinic anhydride, and the upgraded gas stream has a molar hydrogen to CO ratio greater than 5.1.

10. The method of claim 9, wherein and the upgraded gas stream has a hydrogen to CO ratio greater than 10:1, greater than 20:1, greater than 50:1, greater than 100:1, or greater than 1,000:1.

11. The method of claim 9, wherein the upgraded gas stream is substantially free of carbon monoxide.

\* \* \* \* \*